US006905682B2

(12) United States Patent
Gaines et al.

(10) Patent No.: US 6,905,682 B2
(45) Date of Patent: Jun. 14, 2005

(54) FLEA ALLANTOINASE PROTEINS AND USES THEREOF

(75) Inventors: Patrick J. Gaines, Fort Collins, CO (US); Nancy Wisnewski, Fort Collins, CO (US)

(73) Assignee: Heska Corporation, Fort Collins, CO (US)

( * ) Notice: Subject to any disclaimer, the term of this patent is extended or adjusted under 35 U.S.C. 154(b) by 401 days.

(21) Appl. No.: 10/180,165

(22) Filed: Jun. 25, 2002

(65) Prior Publication Data

US 2005/0106565 A1 May 19, 2005

Related U.S. Application Data

(60) Division of application No. 09/894,698, filed on Jun. 28, 2001, now Pat. No. 6,469,152, which is a continuation-in-part of application No. 09/543,668, filed on Apr. 7, 2000, now abandoned.
(60) Provisional application No. 60/128,704, filed on Apr. 9, 1999.

(51) Int. Cl.[7] .......................... A61K 38/46; C12N 9/14; C12N 1/20; C12N 15/00; C07H 21/04
(52) U.S. Cl. .................. 424/94.6; 435/195; 435/252.3; 435/320.1; 536/23.2; 530/300; 530/350
(58) Field of Search .................. 424/94.6; 435/195, 435/252.3, 320.1; 536/23.2; 530/300, 350

(56) References Cited

PUBLICATIONS

Bajjalieh et al., 1993, *Proc. Natl. Acad Sci. USA*, vol. 90, pp. 2150–2154.
Barry et al., 1999, *Insect Biochemistry and Molecular Biology*, 29, pp 319–327.
Bristow et al., 1996, *J Pharmacol Exp Ther*, 279(2), pp 492–501.
Casu et al., 1997, *Proc. Natl. Acad. Sci. USA*, vol. 94, pp 8939–8944.
East et al., 1993, *International Journal for Parasitology*, vol. 23, No 2, pp 221–229.
East et al., 1993, *Immunology and Cell Biology*, 71, pp. 453–462.
Eisemann et al., 1994, *International Journal for Parisitology*, vol. 24, No 1, pp 15–26.
Eisemann et al., 1993, *Medical and Veterinary Entomology*, 7, pp 177–185.
Eldefrawi et al., 1987, *FASEB J.*, vol. 1, No. 4, pp. 262–271.
Elvin et al., 1996, *The Journal of Biological Chemistry*, vol. 271, No 15, pp 8925–8935.
Emery et al., 1998, *Journal of Insect Physiology*, 44, pp. 197–209.
Feany et al., 1992, *Cell*, vol 70, pp. 861–867.
Fujiwara et al., 1995,*Biochem. J.*, 312, pp 315–318.
Gready et al., 1997, *Protein Science*, 6, pp 983–998.

Hayashi et al., 1994, *The Journal of Biological Chemistry*, vol. 269, No 16, pp 12269–12276.
Hendersen et al., 1994,*Insect Biochem. Molec. Biol.*, vol 24, No 4, pp 363–371.
Hosie et al., 1997, *Trends Neurosci.*, vol. 20, pp. 578–583.
Ikeda et al., 1998, *NeuroReport*, vol. 9, No. 14, pp 3189–3195.
Karp et al., 1993, *J Biol Chem*, 268(5), pp 3728–3733.
Kim et al., 1998, *Biochem. J.*, 330, pp 295–302.
Koenderink et al., 1999, *The Journal of Biological Chemistry*, vol 274, No 17, pp 11604–11610.
Landry et al., 1994, *The Journal of Biological Chemistry*, vol. 268, No. 20, pp. 14948–14955.
Ma et al., 1999, *Molecular Brain Research*, 63, pp 217–224.
McKenna et al., 1994, *The Journal of Biological Chemistry*, vol 269, No 23, pp 16340–16347.
O'Donnell et al, 1998, *American Journal of Physiology*, vol. 274, Issue 4, No. 2, pp. R1039–R1049.
Orgad et al., ,1998 *J Exp Biol*, 201, pp 115–120.
Ozaki et al., 1995, *Eur. J. Biochem.*, 230, pp 298–308.
Planells–Cases et al., 1993, *Proc Natl Acad Sci USA*, 90(11), pp 5057–5061.
Pruett, J., 1999, *International Journal for Parasitology*, 29, pp 25–32.
Ramasamy et al., 1996, *J. Med. Entomol.*, vol 33, No 1, pp 162–164.
Ramasamy et al., 1997, *Biochimica et Biophysica Acta*, 1361, pp 114–122.
Reeves et al., 1993, *Insect Biochem. Molec. Biol.*, vol. 23, No. 7, pp. 809–814.
Romanov et al., 1999, *Analytical Biochemistry*, 268, pp 49–53.
Schnee et al., 1997, *The Journal of Experimental Biology*, 200, pp 2947–2955.
Schorderet et al., 1998, *Insect Biochem. Molec. Biol.*, vol 28, No 2, pp 99–111.
Schubert, K., 1981, *Plant Physiol.*, 68, pp 1115–1122.
Shen et al., 1998, *The Journal of Biological Chemistry*, vol.273, No 28, pp 17665–17670.
Srikrishnaraj et al., 1995, *Medical and Veterinary Entomology*, 9, pp 353–357.
Sun et al., 1998, *Journal of Neurochemistry*, vol. 71, No. 1, pp. 142–151.

(Continued)

*Primary Examiner*—Tekchand Saidha
(74) *Attorney, Agent, or Firm*—Heska Corporation

(57) ABSTRACT

The present invention relates to flea allantoinase proteins; to flea allantoinase nucleic acid molecules, including those that encode such flea allantoinase proteins; to antibodies raised against such proteins; and to compounds that inhibit the activity of such proteins. The present invention also includes methods to obtain such proteins, nucleic acid molecules, antibodies, and inhibitory compounds. The present invention also includes therapeutic compositions comprising such inhibitory compounds, particularly those that specifically inhibit flea allantoinase activity, as well as the use of such therapeutic compositions to treat animals.

16 Claims, No Drawings

OTHER PUBLICATIONS

Tellam et al., 1999, *Insect Biochemistry and Molecular Biology*, 29, pp 87–101.

Thiemann et al., 1992, *Nature*, vol. 356, pp. 57–60.

Thymianou et al., 1998, *Insect Molecular Biology*, 7(4), pp. 345–353.

Tingley et al., 1993, *Nature*, vol 364, pp 70–73.

Usuda et al., 1994, *Journal of Cell Science*, 107, pp. 1073–1081.

Wang et al., 1998, *Archives of Biochemistry and Biophysics*, vol 358, No 1, pp 116–124.

Wang et al., 1998, *Insect Molecular Biology*, 7(4), pp 317–325.

Westphal et al.1999, *Cell*, vol. 96, 689–700.

Wijffels et al.1999, *International Journal for Parasitology*, 29, pp 1363–1377.

Younkin et al., 1993, *Proc Natl Acad Sci USA*, 90, pp 2174–2178.

Attwood, Teresa K., 2000, *Science*, vol 290, pp. 471–473.

Gerhold et al., 1996, *BioEssays*, vol. 18, No. 12, pp. 973–981.

Russell et al., 1994, *J. Mol. Biol.*, 244, pp. 332–350.

Wells et al., 1997, *Journal of Leukocyte Biology*, vol. 61, pp. 545–550.

SEQUENCE LISTING

```
<160> NUMBER OF SEQ ID NOS: 15

<210> SEQ ID NO 1
<211> LENGTH: 2035
<212> TYPE: DNA
<213> ORGANISM: Ctenocephalides felis
<220> FEATURE:
<221> NAME/KEY: CDS
<222> LOCATION: (152)..(1600)

<400> SEQUENCE: 1
aacataataa taacttaata aaattttgtg atcagatttc taatatccag aacaaagcca        60
gtaattataa gaaccaagcc tatttcatgt gaaggttact tctccacagt attattatct       120
atctcaagaa gtaatctatt actgaatcaa a atg aaa agc agt acc tgt att          172
                                   Met Lys Ser Ser Thr Cys Ile
                                     1               5 ttt ctt ctg gtc att atg ctg aat tgc aag aac ctt gtt aat gct gcg        220
Phe Leu Leu Val Ile Met Leu Asn Cys Lys Asn Leu Val Asn Ala Ala
         10                  15                  20 tgc acc aac aac gcg cct cca atg aag ata ttc cgt agc cga aga gtt        268
Cys Thr Asn Asn Ala Pro Pro Met Lys Ile Phe Arg Ser Arg Arg Val
     25                  30                  35 ctt ctc ggt gat ggt act gaa aga gat gct ggc att gta gtt gat tcc        316
Leu Leu Gly Asp Gly Thr Glu Arg Asp Ala Gly Ile Val Val Asp Ser
 40                  45                  50                  55 tcc gga aga ata aaa agt ata att tca gga gaa gaa gtg gaa agg ata        364
Ser Gly Arg Ile Lys Ser Ile Ile Ser Gly Glu Glu Val Glu Arg Ile
                     60                  65                  70 gct aac gaa act aaa gtt gag gtg ttg gac tac ggt caa ttt tca ata        412
Ala Asn Glu Thr Lys Val Glu Val Leu Asp Tyr Gly Gln Phe Ser Ile
                 75                  80                  85 tgg cca ggt gtg ata gac tct cat gtg cac gtc aac gaa cca gga aga        460
Trp Pro Gly Val Ile Asp Ser His Val His Val Asn Glu Pro Gly Arg
             90                  95                 100 gaa tcc tgg gaa gga tac acc aca gct act aaa gca gca gct tgg ggc        508
Glu Ser Trp Glu Gly Tyr Thr Thr Ala Thr Lys Ala Ala Ala Trp Gly
        105                 110                 115 ggg att acc aca ata gta gac atg cct ttg aat tcc atc cca cct aca        556
Gly Ile Thr Thr Ile Val Asp Met Pro Leu Asn Ser Ile Pro Pro Thr
120                 125                 130                 135 act act gta gag aat ttg aga aca aaa gtg aat tca gcc tgt ggt aaa        604
Thr Thr Val Glu Asn Leu Arg Thr Lys Val Asn Ser Ala Cys Gly Lys
                    140                 145                 150 acg cat gtt gat gtc gct ttc tgg gga ggc gtg att cct ggc aat gcg        652
Thr His Val Asp Val Ala Phe Trp Gly Gly Val Ile Pro Gly Asn Ala
                155                 160                 165 cac gaa ttg ttg cca ctt atc aac gcc gga gta aga gga ttc aaa tgt        700
```

-continued

```
His Glu Leu Leu Pro Leu Ile Asn Ala Gly Val Arg Gly Phe Lys Cys
        170                 175                 180 ttt aca agt gaa agt ggt gtc gat gag ttt cca cag gtt act aaa aat       748
Phe Thr Ser Glu Ser Gly Val Asp Glu Phe Pro Gln Val Thr Lys Asn
    185                 190                 195 gat ctg gaa atg gct cta aaa gag ctc cag aaa gca aat tcc gta ctt       796
Asp Leu Glu Met Ala Leu Lys Glu Leu Gln Lys Ala Asn Ser Val Leu
200                 205                 210                 215 ctg tac cat gcc gaa tta ccc gct cct caa gaa aat gtt aca agc aat       844
Leu Tyr His Ala Glu Leu Pro Ala Pro Gln Glu Asn Val Thr Ser Asn
            220                 225                 230 gaa act gaa aag tac atg act tac ctg aaa aca cga cct cca agt atg       892
Glu Thr Glu Lys Tyr Met Thr Tyr Leu Lys Thr Arg Pro Pro Ser Met
        235                 240                 245 gaa gta aat gct att gat atg att ata gac ctc aca aaa aaa tat aaa       940
Glu Val Asn Ala Ile Asp Met Ile Ile Asp Leu Thr Lys Lys Tyr Lys
    250                 255                 260 gtt agg tct cac ata gtg cat cta tca gca gca ggt gct tta ccg caa       988
Val Arg Ser His Ile Val His Leu Ser Ala Ala Gly Ala Leu Pro Gln
265                 270                 275 ttg aaa aaa gcg cgc tca gag aac gtt cca ctt tcg att gaa act tgt      1036
Leu Lys Lys Ala Arg Ser Glu Asn Val Pro Leu Ser Ile Glu Thr Cys
280                 285                 290                 295 cat cat tac tta acc ttt gct gct gaa gat gtt cca gat gga cat act      1084
His His Tyr Leu Thr Phe Ala Ala Glu Asp Val Pro Asp Gly His Thr
            300                 305                 310 gaa tac aaa tgc gct cca cca att aga gaa gaa agt aat caa gaa aaa      1132
Glu Tyr Lys Cys Ala Pro Pro Ile Arg Glu Glu Ser Asn Gln Glu Lys
        315                 320                 325 tta tgg caa gct ttg gaa aac aga gat att gat atg gta gtc agt gat      1180
Leu Trp Gln Ala Leu Glu Asn Arg Asp Ile Asp Met Val Val Ser Asp
    330                 335                 340 cat tct cca tca cct gct gca ctg aaa ggc ctg tgc aat ggt tgt cat      1228
His Ser Pro Ser Pro Ala Ala Leu Lys Gly Leu Cys Asn Gly Cys His
345                 350                 355 cct gat ttc cta aaa gct tgg ggt gga att gct ggt atg cag ttt gga      1276
Pro Asp Phe Leu Lys Ala Trp Gly Gly Ile Ala Gly Met Gln Phe Gly
360                 365                 370                 375 tta tct tta ata agg acc ggt gct tct aaa aga ggc ttt aaa gct cat      1324
Leu Ser Leu Ile Arg Thr Gly Ala Ser Lys Arg Gly Phe Lys Ala His
            380                 385                 390 gat gta tct cgt tta tta tct gcg gga cct gcg aaa tta act gga ctg      1372
Asp Val Ser Arg Leu Leu Ser Ala Gly Pro Ala Lys Leu Thr Gly Leu
        395                 400                 405 gat ggc ata aaa gga caa atc aaa gaa ggc ttg gat gct gat tta gta      1420
Asp Gly Ile Lys Gly Gln Ile Lys Glu Gly Leu Asp Ala Asp Leu Val
    410                 415                 420 att tgg gat cct gag gaa gaa ttt aag gtc act aaa gac ata atc caa      1468
Ile Trp Asp Pro Glu Glu Glu Phe Lys Val Thr Lys Asp Ile Ile Gln
425                 430                 435 cac aag aat aaa gaa aca cca tac tta gga atg acg ttg aag ggc aaa      1516
His Lys Asn Lys Glu Thr Pro Tyr Leu Gly Met Thr Leu Lys Gly Lys
440                 445                 450                 455 gtt cat gca act gtt gta cga gga gac ttt gtt tac cgt aat gga caa      1564
Val His Ala Thr Val Val Arg Gly Asp Phe Val Tyr Arg Asn Gly Gln
            460                 465                 470 cca ttc gaa att cca aaa gga aat tta ctt att gaa tgattaaatg            1610
Pro Phe Glu Ile Pro Lys Gly Asn Leu Leu Ile Glu
        475                 480
```

-continued

```
taatagatta atcaaatttt agatgattaa aattgtttta ttactacaat agcaacctct    1670
gcctgaaaat taaccgaaca aacttctaac atccttatta atgtatagat tttgaataat    1730
aacatagaaa ttatactatt tttttgatga ctctaataaa aaaatgtat aaatggccat     1790 gcctgatata ttttgataa ccttaatgaa aaaatgttta aatggccatg tctgaaaaga    1850
tttctatgtg tatttttttg ttaacatttt attgttgaat ggataaaaga taaatacaat    1910
tttataagct gtttggataa attaattttg aataaatcca taatcataga atatgttaag    1970
tagcaaatta aaatatggac cacaaaccac aaaatgtata cgaaatataa cttatatgat    2030
atatg                                                                2035
```

<210> SEQ ID NO 2
<211> LENGTH: 483
<212> TYPE: PRT
<213> ORGANISM: Ctenocephalides felis

<400> SEQUENCE: 2

```
Met Lys Ser Ser Thr Cys Ile Phe Leu Leu Val Ile Met Leu Asn Cys
  1               5                  10                  15

Lys Asn Leu Val Asn Ala Ala Cys Thr Asn Ala Pro Pro Met Lys
             20                  25                  30

Ile Phe Arg Ser Arg Arg Val Leu Leu Gly Asp Gly Thr Glu Arg Asp
         35                  40                  45

Ala Gly Ile Val Val Asp Ser Ser Gly Arg Ile Lys Ser Ile Ile Ser
     50                  55                  60

Gly Glu Glu Val Glu Arg Ile Ala Asn Glu Thr Lys Val Glu Val Leu
 65                  70                  75                  80

Asp Tyr Gly Gln Phe Ser Ile Trp Pro Gly Val Ile Asp Ser His Val
                 85                  90                  95

His Val Asn Glu Pro Gly Arg Glu Ser Trp Glu Gly Tyr Thr Thr Ala
            100                 105                 110

Thr Lys Ala Ala Ala Trp Gly Gly Ile Thr Thr Ile Val Asp Met Pro
        115                 120                 125

Leu Asn Ser Ile Pro Pro Thr Thr Thr Val Glu Asn Leu Arg Thr Lys
    130                 135                 140

Val Asn Ser Ala Cys Gly Lys Thr His Val Asp Val Ala Phe Trp Gly
145                 150                 155                 160

Gly Val Ile Pro Gly Asn Ala His Glu Leu Leu Pro Leu Ile Asn Ala
                165                 170                 175

Gly Val Arg Gly Phe Lys Cys Phe Thr Ser Glu Ser Gly Val Asp Glu
            180                 185                 190

Phe Pro Gln Val Thr Lys Asn Asp Leu Glu Met Ala Leu Lys Glu Leu
        195                 200                 205

Gln Lys Ala Asn Ser Val Leu Leu Tyr His Ala Glu Leu Pro Ala Pro
    210                 215                 220

Gln Glu Asn Val Thr Ser Asn Glu Thr Glu Lys Tyr Met Thr Tyr Leu
225                 230                 235                 240

Lys Thr Arg Pro Pro Ser Met Glu Val Asn Ala Ile Asp Met Ile Ile
                245                 250                 255

Asp Leu Thr Lys Lys Tyr Lys Val Arg Ser His Ile Val His Leu Ser
            260                 265                 270

Ala Ala Gly Ala Leu Pro Gln Leu Lys Lys Ala Arg Ser Glu Asn Val
        275                 280                 285

Pro Leu Ser Ile Glu Thr Cys His His Tyr Leu Thr Phe Ala Ala Glu
```

-continued

```
                    290                 295                 300
Asp Val Pro Asp Gly His Thr Glu Tyr Lys Cys Ala Pro Pro Ile Arg
305                 310                 315                 320

Glu Glu Ser Asn Gln Glu Lys Leu Trp Gln Ala Leu Glu Asn Arg Asp
                325                 330                 335

Ile Asp Met Val Val Ser Asp His Ser Pro Ser Pro Ala Ala Leu Lys
                340                 345                 350

Gly Leu Cys Asn Gly Cys His Pro Asp Phe Leu Lys Ala Trp Gly Gly
            355                 360                 365

Ile Ala Gly Met Gln Phe Gly Leu Ser Leu Ile Arg Thr Gly Ala Ser
370                 375                 380

Lys Arg Gly Phe Lys Ala His Asp Val Ser Arg Leu Ser Ala Gly
385                 390                 395                 400

Pro Ala Lys Leu Thr Gly Leu Asp Gly Ile Lys Gly Gln Ile Lys Glu
                405                 410                 415

Gly Leu Asp Ala Asp Leu Val Ile Trp Asp Pro Glu Glu Phe Lys
                420                 425                 430

Val Thr Lys Asp Ile Ile Gln His Lys Asn Lys Glu Thr Pro Tyr Leu
                435                 440                 445

Gly Met Thr Leu Lys Gly Lys Val His Ala Thr Val Val Arg Gly Asp
450                 455                 460

Phe Val Tyr Arg Asn Gly Gln Pro Phe Glu Ile Pro Lys Gly Asn Leu
465                 470                 475                 480

Leu Ile Glu
```

<210> SEQ ID NO 3
<211> LENGTH: 2035
<212> TYPE: DNA
<213> ORGANISM: Ctenocephalides felis

<400> SEQUENCE: 3

```
catatatcat ataagttata tttcgtatac attttgtggt ttgtggtcca tattttaatt    60
tgctacttaa catattctat gattatggat ttattcaaaa ttaatttatc caaacagctt   120
ataaaattgt atttatcttt tatccattca acaataaaat gttaacaaaa aaatacacat   180
agaaatcttt tcagacatgg ccatttaaac attttttcat taaggttatc aaaaatatat   240
caggcatggc catttataca tttttttat tagagtcatc aaaaaaatag tataatttct   300
atgttattat tcaaaatcta tacattaata aggatgttag aagtttgttc ggttaatttt   360
caggcagagg ttgctattgt agtaataaaa caatttaat catctaaaat ttgattaatc   420
tattacattt aatcattcaa taagtaaatt tccttttgga atttcgaatg gttgtccatt   480
acggtaaaca aagtctcctc gtacaacagt tgcatgaact ttgcccttca acgtcattcc   540
taagtatggt gtttctttat tcttgtgttg gattatgtct ttagtgacct taaattcttc   600
ctcaggatcc caaattacta atcagcatc caagccttct ttgatttgtc cttttatgcc   660
atccagtcca gttaatttcg caggtcccgc agataataaa cgagatacat catgagcttt   720
aaagcctctt ttagaagcac cggtccttat taaagataat ccaaactgca taccagcaat   780
tccaccccaa gctttagga aatcaggatg acaaccattg cacaggcctt tcagtgcagc   840
aggtgatgga gaatgatcac tgactaccat atcaatatct ctgttttcca aagcttgcca   900
taatttttct tgattacttt cttctctaat tggtggagcg catttgtatt cagtatgtcc   960
atctggaaca tcttcagcag caaaggttaa gtaatgatga caagtttcaa tcgaaagtgg  1020
```

-continued

| | | |
|---|---|---|
| aacgttctct gagcgcgctt ttttcaattg cggtaaagca cctgctgctg atagatgcac | 1080 |
| tatgtgagac ctaactttat atttttttgt gaggtctata atcatatcaa tagcatttac | 1140 |
| ttccatactt ggaggtcgtg ttttcaggta agtcatgtac ttttcagttt cattgcttgt | 1200 |
| aacatttct tgaggagcgg gtaattcggc atggtacaga agtacggaat ttgctttctg | 1260 |
| gagctctttt agagccattt ccagatcatt tttagtaacc tgtggaaact catcgacacc | 1320 |
| actttcactt gtaaaacatt tgaatcctct tactccggcg ttgataagtg gcaacaattc | 1380 |
| gtgcgcattg ccaggaatca cgcctcccca gaaagcgaca tcaacatgcg ttttaccaca | 1440 |
| ggctgaattc acttttgttc tcaaattctc tacagtagtt gtaggtggga tggaattcaa | 1500 |
| aggcatgtct actattgtgg taatcccgcc ccaagctgct gctttagtag ctgtggtgta | 1560 |
| tccttcccag gattctcttc ctggttcgtt gacgtgcaca tgagagtcta tcacacctgg | 1620 |
| ccatattgaa aattgaccgt agtccaacac ctcaacttta gtttcgttag ctatcctttc | 1680 |
| cacttcttct cctgaaatta tacttttttat tcttccggag gaatcaacta caatgccagc | 1740 |
| atctcttca gtaccatcac cgagaagaac tcttcggcta cggaatatct tcattggagg | 1800 |
| cgcgttgttg gtgcacgcag cattaacaag gttcttgcaa ttcagcataa tgaccagaag | 1860 |
| aaaaatacag gtactgcttt tcattttgat tcagtaatag attacttctt gagatagata | 1920 |
| ataatactgt ggagaagtaa ccttcacatg aaataggctt ggttcttata attactggct | 1980 |
| ttgttctgga tattagaaat ctgatcacaa aattttatta agttattatt atgtt | 2035 |

<210> SEQ ID NO 4
<211> LENGTH: 1449
<212> TYPE: DNA
<213> ORGANISM: Ctenocephalides felis

<400> SEQUENCE: 4

| | | |
|---|---|---|
| atgaaaagca gtacctgtat ttttcttctg gtcattatgc tgaattgcaa gaaccttgtt | 60 |
| aatgctgcgt gcaccaacaa cgcgcctcca atgaagatat tccgtagccg aagagttctt | 120 |
| ctcggtgatg gtactgaaag agatgctggc attgtagttg attcctccgg aagaataaaa | 180 |
| agtataattt caggagaaga agtggaaagg atagctaacg aaactaaagt tgaggtgttg | 240 |
| gactacggtc aattttcaat atggccaggt gtgatagact ctcatgtgca cgtcaacgaa | 300 |
| ccaggaagag aatcctggga aggatacacc acagctacta aagcagcagc ttggggcggg | 360 |
| attaccacaa tagtagacat gcctttgaat tccatcccac ctacaactac tgtagagaat | 420 |
| tgagaacaa aagtgaattc agcctgtggt aaaacgcatg ttgatgtcgc tttctgggga | 480 |
| ggcgtgattc ctggcaatgc gcacgaattg ttgccactta tcaacgccgg agtaagagga | 540 |
| ttcaaatgtt ttacaagtga agtggtgtc gatgagtttc cacaggttac taaaaatgat | 600 |
| ctggaaatgg ctctaaaaga gctccagaaa gcaaattccg tacttctgta ccatgccgaa | 660 |
| ttacccgctc tcaagaaaa tgttacaagc aatgaaactg aaaagtacat gacttacctg | 720 |
| aaaacacgac ctccaagtat ggaagtaaat gctattgata tgattataga cctcacaaaa | 780 |
| aaatataaag ttaggtctca catagtgcat ctatcagcag caggtgcttt accgcaattg | 840 |
| aaaaaagcgc gctcagagaa cgttccactt tcgattgaaa cttgtcatca ttacttaacc | 900 |
| tttgctgctg aagatgttcc agatggacat actgaataca aatgcgctcc accaattaga | 960 |
| gaagaaagta atcaagaaaa attatggcaa gctttggaaa acagagatat tgatatggta | 1020 |
| gtcagtgatc attctccatc acctgctgca ctgaaaggcc tgtgcaatgg ttgtcatcct | 1080 |
| gatttcctaa aagcttgggg tggaattgct ggtatgcagt ttggattatc tttaataagg | 1140 |

-continued

```
accggtgctt ctaaaagagg ctttaaagct catgatgtat ctcgtttatt atctgcggga      1200
cctgcgaaat taactggact ggatggcata aaggacaaa tcaaagaagg cttggatgct       1260
gatttagtaa tttgggatcc tgaggaagaa tttaaggtca ctaaagacat aatccaacac      1320
aagaataaag aaacaccata cttaggaatg acgttgaagg gcaaagttca tgcaactgtt     1380
gtacgaggag actttgttta ccgtaatgga caaccattcg aaattccaaa aggaaattta     1440
cttattgaa                                                              1449

<210> SEQ ID NO 5
<211> LENGTH: 1449
<212> TYPE: DNA
<213> ORGANISM: Ctenocephalides felis

<400> SEQUENCE: 5
ttcaataagt aaatttcctt ttggaatttc gaatggttgt ccattacggt aaacaaagtc       60
tcctcgtaca acagttgcat gaactttgcc cttcaacgtc attcctaagt atggtgtttc      120
tttattcttg tgttggatta tgtctttagt gaccttaaat tcttcctcag gatcccaaat     180
tactaaatca gcatccaagc cttctttgat ttgtcctttt atgccatcca gtccagttaa      240
tttcgcaggt cccgcagata taaacgaga tacatcatga gctttaaagc ctcttttaga       300
agcaccggtc cttattaaag ataatccaaa ctgcatacca gcaattccac cccaagcttt      360
taggaaatca ggatgacaac cattgcacag gcctttcagt gcagcaggtg atggagaatg      420
atcactgact accatatcaa tatctctgtt tccaaagct tgccataatt tttcttgatt      480
actttcttct ctaattggtg gagcgcattt gtattcagta tgtccatctg gaacatcttc      540
agcagcaaag gttaagtaat gatgacaagt ttcaatcgaa agtggaacgt tctctgagcg      600
cgcttttttc aattgcggta aagcacctgc tgctgataga tgcactatgt gagacctaac      660
tttatatttt tttgtgaggt ctataatcat atcaatagca tttacttcca tacttggagg      720
tcgtgttttc aggtaagtca tgtactttc agtttcattg cttgtaacat ttcttgagg       780 agcgggtaat tcggcatggt acagaagtac ggaatttgct ttctggagct cttttagagc      840
catttccaga tcatttttag taacctgtgg aaactcatcg acaccacttt cacttgtaaa      900
acatttgaat cctcttactc cggcgttgat aagtggcaac aattcgtgcg cattgccagg      960
aatcacgcct ccccagaaag cgacatcaac atgcgtttta ccacaggctg aattcacttt     1020
tgttctcaaa ttctctacag tagttgtagg tgggatggaa ttcaaaggca tgtctactat     1080
tgtggtaatc ccgccccaag ctgctgcttt agtagctgtg gtgtatcctt cccaggattc      1140
tcttcctggt tcgttgacgt gcacatgaga gtctatcaca cctggccata ttgaaaattg     1200
accgtagtcc aacacctcaa ctttagtttc gttagctatc ctttccactt cttctcctga     1260
aattatactt tttattcttc cggaggaatc aactacaatg ccagcatctc tttcagtacc     1320
atcaccgaga agaactcttc ggctacggaa tatcttcatt ggaggcgcgt tgttggtgca     1380
cgcagcatta acaaggttct tgcaattcag cataatgacc agaagaaaaa tacaggtact     1440
gcttttcat                                                              1449

<210> SEQ ID NO 6
<211> LENGTH: 1383
<212> TYPE: DNA
<213> ORGANISM: Ctenocephalides felis
<220> FEATURE:
<221> NAME/KEY: CDS
<222> LOCATION: (1)..(1383)
```

<400> SEQUENCE: 6

| | | | | | | | | | | | | | | | | |
|---|---|---|---|---|---|---|---|---|---|---|---|---|---|---|---|---|
| gcg | tgc | acc | aac | aac | gcg | cct | cca | atg | aag | ata | ttc | cgt | agc | cga | aga | 48 |
| Ala | Cys | Thr | Asn | Asn | Ala | Pro | Pro | Met | Lys | Ile | Phe | Arg | Ser | Arg | Arg | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gtt | ctt | ctc | ggt | gat | ggt | act | gaa | aga | gat | gct | ggc | att | gta | gtt | gat | 96 |
| Val | Leu | Leu | Gly | Asp | Gly | Thr | Glu | Arg | Asp | Ala | Gly | Ile | Val | Val | Asp | |
| | | | 20 | | | | | 25 | | | | | 30 | | | |

| | | | | | | | | | | | | | | | | |
|---|---|---|---|---|---|---|---|---|---|---|---|---|---|---|---|---|
| tcc | tcc | gga | aga | ata | aaa | agt | ata | att | tca | gga | gaa | gaa | gtg | gaa | agg | 144 |
| Ser | Ser | Gly | Arg | Ile | Lys | Ser | Ile | Ile | Ser | Gly | Glu | Glu | Val | Glu | Arg | |
| | | 35 | | | | | 40 | | | | | 45 | | | | |

| | | | | | | | | | | | | | | | | |
|---|---|---|---|---|---|---|---|---|---|---|---|---|---|---|---|---|
| ata | gct | aac | gaa | act | aaa | gtt | gag | gtg | ttg | gac | tac | ggt | caa | ttt | tca | 192 |
| Ile | Ala | Asn | Glu | Thr | Lys | Val | Glu | Val | Leu | Asp | Tyr | Gly | Gln | Phe | Ser | |
| 50 | | | | | 55 | | | | | 60 | | | | | | |

| | | | | | | | | | | | | | | | | |
|---|---|---|---|---|---|---|---|---|---|---|---|---|---|---|---|---|
| ata | tgg | cca | ggt | gtg | ata | gac | tct | cat | gtg | cac | gtc | aac | gaa | cca | gga | 240 |
| Ile | Trp | Pro | Gly | Val | Ile | Asp | Ser | His | Val | His | Val | Asn | Glu | Pro | Gly | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| aga | gaa | tcc | tgg | gaa | gga | tac | acc | aca | gct | act | aaa | gca | gca | gct | tgg | 288 |
| Arg | Glu | Ser | Trp | Glu | Gly | Tyr | Thr | Thr | Ala | Thr | Lys | Ala | Ala | Ala | Trp | |
| | | | | 85 | | | | | 90 | | | | | 95 | | |

| | | | | | | | | | | | | | | | | |
|---|---|---|---|---|---|---|---|---|---|---|---|---|---|---|---|---|
| ggc | ggg | att | acc | aca | ata | gta | gac | atg | cct | ttg | aat | tcc | atc | cca | cct | 336 |
| Gly | Gly | Ile | Thr | Thr | Ile | Val | Asp | Met | Pro | Leu | Asn | Ser | Ile | Pro | Pro | |
| | | | 100 | | | | | 105 | | | | | 110 | | | |

| | | | | | | | | | | | | | | | | |
|---|---|---|---|---|---|---|---|---|---|---|---|---|---|---|---|---|
| aca | act | act | gta | gag | aat | ttg | aga | aca | aaa | gtg | aat | tca | gcc | tgt | ggt | 384 |
| Thr | Thr | Thr | Val | Glu | Asn | Leu | Arg | Thr | Lys | Val | Asn | Ser | Ala | Cys | Gly | |
| | | | 115 | | | | | 120 | | | | | 125 | | | |

| | | | | | | | | | | | | | | | | |
|---|---|---|---|---|---|---|---|---|---|---|---|---|---|---|---|---|
| aaa | acg | cat | gtt | gat | gtc | gct | ttc | tgg | gga | ggc | gtg | att | cct | ggc | aat | 432 |
| Lys | Thr | His | Val | Asp | Val | Ala | Phe | Trp | Gly | Gly | Val | Ile | Pro | Gly | Asn | |
| 130 | | | | | 135 | | | | | 140 | | | | | | |

| | | | | | | | | | | | | | | | | |
|---|---|---|---|---|---|---|---|---|---|---|---|---|---|---|---|---|
| gcg | cac | gaa | ttg | ttg | cca | ctt | atc | aac | gcc | gga | gta | aga | gga | ttc | aaa | 480 |
| Ala | His | Glu | Leu | Leu | Pro | Leu | Ile | Asn | Ala | Gly | Val | Arg | Gly | Phe | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tgt | ttt | aca | agt | gaa | agt | ggt | gtc | gat | gag | ttt | cca | cag | gtt | act | aaa | 528 |
| Cys | Phe | Thr | Ser | Glu | Ser | Gly | Val | Asp | Glu | Phe | Pro | Gln | Val | Thr | Lys | |
| | | | | 165 | | | | | 170 | | | | | 175 | | |

| | | | | | | | | | | | | | | | | |
|---|---|---|---|---|---|---|---|---|---|---|---|---|---|---|---|---|
| aat | gat | ctg | gaa | atg | gct | cta | aaa | gag | ctc | cag | aaa | gca | aat | tcc | gta | 576 |
| Asn | Asp | Leu | Glu | Met | Ala | Leu | Lys | Glu | Leu | Gln | Lys | Ala | Asn | Ser | Val | |
| | | | 180 | | | | | 185 | | | | | 190 | | | |

| | | | | | | | | | | | | | | | | |
|---|---|---|---|---|---|---|---|---|---|---|---|---|---|---|---|---|
| ctt | ctg | tac | cat | gcc | gaa | tta | ccc | gct | cct | caa | gaa | aat | gtt | aca | agc | 624 |
| Leu | Leu | Tyr | His | Ala | Glu | Leu | Pro | Ala | Pro | Gln | Glu | Asn | Val | Thr | Ser | |
| | | | 195 | | | | | 200 | | | | | 205 | | | |

| | | | | | | | | | | | | | | | | |
|---|---|---|---|---|---|---|---|---|---|---|---|---|---|---|---|---|
| aat | gaa | act | gaa | aag | tac | atg | act | tac | ctg | aaa | aca | cga | cct | cca | agt | 672 |
| Asn | Glu | Thr | Glu | Lys | Tyr | Met | Thr | Tyr | Leu | Lys | Thr | Arg | Pro | Pro | Ser | |
| | | 210 | | | | | 215 | | | | | 220 | | | | |

| | | | | | | | | | | | | | | | | |
|---|---|---|---|---|---|---|---|---|---|---|---|---|---|---|---|---|
| atg | gaa | gta | aat | gct | att | gat | atg | att | ata | gac | ctc | aca | aaa | aaa | tat | 720 |
| Met | Glu | Val | Asn | Ala | Ile | Asp | Met | Ile | Ile | Asp | Leu | Thr | Lys | Lys | Tyr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aaa | gtt | agg | tct | cac | ata | gtg | cat | cta | tca | gca | gca | ggt | gct | tta | ccg | 768 |
| Lys | Val | Arg | Ser | His | Ile | Val | His | Leu | Ser | Ala | Ala | Gly | Ala | Leu | Pro | |
| | | | | 245 | | | | | 250 | | | | | 255 | | |

| | | | | | | | | | | | | | | | | |
|---|---|---|---|---|---|---|---|---|---|---|---|---|---|---|---|---|
| caa | ttg | aaa | aaa | gcg | cgc | tca | gag | aac | gtt | cca | ctt | tcg | att | gaa | act | 816 |
| Gln | Leu | Lys | Lys | Ala | Arg | Ser | Glu | Asn | Val | Pro | Leu | Ser | Ile | Glu | Thr | |
| | | | | 260 | | | | | 265 | | | | | 270 | | |

| | | | | | | | | | | | | | | | | |
|---|---|---|---|---|---|---|---|---|---|---|---|---|---|---|---|---|
| tgt | cat | cat | tac | tta | acc | ttt | gct | gct | gaa | gat | gtt | cca | gat | gga | cat | 864 |
| Cys | His | His | Tyr | Leu | Thr | Phe | Ala | Ala | Glu | Asp | Val | Pro | Asp | Gly | His | |
| | | 275 | | | | | 280 | | | | | 285 | | | | |

| | | | | | | | | | | | | | | | | |
|---|---|---|---|---|---|---|---|---|---|---|---|---|---|---|---|---|
| act | gaa | tac | aaa | tgc | gct | cca | cca | att | aga | gaa | gaa | agt | aat | caa | gaa | 912 |
| Thr | Glu | Tyr | Lys | Cys | Ala | Pro | Pro | Ile | Arg | Glu | Glu | Ser | Asn | Gln | Glu | |
| | | 290 | | | | | 295 | | | | | 300 | | | | |

```
aaa tta tgg caa gct ttg gaa aac aga gat att gat atg gta gtc agt      960
Lys Leu Trp Gln Ala Leu Glu Asn Arg Asp Ile Asp Met Val Val Ser
305                 310                 315                 320 gat cat tct cca tca cct gct gca ctg aaa ggc ctg tgc aat ggt tgt     1008
Asp His Ser Pro Ser Pro Ala Ala Leu Lys Gly Leu Cys Asn Gly Cys
                325                 330                 335 cat cct gat ttc cta aaa gct tgg ggt gga att gct ggt atg cag ttt     1056
His Pro Asp Phe Leu Lys Ala Trp Gly Gly Ile Ala Gly Met Gln Phe
            340                 345                 350 gga tta tct tta ata agg acc ggt gct tct aaa aga ggc ttt aaa gct     1104
Gly Leu Ser Leu Ile Arg Thr Gly Ala Ser Lys Arg Gly Phe Lys Ala
        355                 360                 365 cat gat gta tct cgt tta tta tct gcg gga cct gcg aaa tta act gga     1152
His Asp Val Ser Arg Leu Leu Ser Ala Gly Pro Ala Lys Leu Thr Gly
370                 375                 380 ctg gat ggc ata aaa gga caa atc aaa gaa ggc ttg gat gct gat tta     1200
Leu Asp Gly Ile Lys Gly Gln Ile Lys Glu Gly Leu Asp Ala Asp Leu
385                 390                 395                 400 gta att tgg gat cct gag gaa gaa ttt aag gtc act aaa gac ata atc     1248
Val Ile Trp Asp Pro Glu Glu Glu Phe Lys Val Thr Lys Asp Ile Ile
                405                 410                 415 caa cac aag aat aaa gaa aca cca tac tta gga atg acg ttg aag ggc     1296
Gln His Lys Asn Lys Glu Thr Pro Tyr Leu Gly Met Thr Leu Lys Gly
            420                 425                 430 aaa gtt cat gca act gtt gta cga gga gac ttt gtt tac cgt aat gga     1344
Lys Val His Ala Thr Val Val Arg Gly Asp Phe Val Tyr Arg Asn Gly
        435                 440                 445 caa cca ttc gaa att cca aaa gga aat tta ctt att gaa                 1383
Gln Pro Phe Glu Ile Pro Lys Gly Asn Leu Leu Ile Glu
    450                 455                 460

<210> SEQ ID NO 7
<211> LENGTH: 461
<212> TYPE: PRT
<213> ORGANISM: Ctenocephalides felis

<400> SEQUENCE: 7

Ala Cys Thr Asn Asn Ala Pro Pro Met Lys Ile Phe Arg Ser Arg Arg
 1               5                  10                  15

Val Leu Leu Gly Asp Gly Thr Glu Arg Asp Ala Gly Ile Val Val Asp
            20                  25                  30

Ser Ser Gly Arg Ile Lys Ser Ile Ile Ser Gly Glu Glu Val Glu Arg
        35                  40                  45

Ile Ala Asn Glu Thr Lys Val Glu Val Leu Asp Tyr Gly Gln Phe Ser
    50                  55                  60

Ile Trp Pro Gly Val Ile Asp Ser His Val His Val Asn Glu Pro Gly
65                  70                  75                  80

Arg Glu Ser Trp Glu Gly Tyr Thr Thr Ala Thr Lys Ala Ala Trp
                85                  90                  95

Gly Gly Ile Thr Thr Ile Val Asp Met Pro Leu Asn Ser Ile Pro Pro
            100                 105                 110

Thr Thr Thr Val Glu Asn Leu Arg Thr Lys Val Asn Ser Ala Cys Gly
        115                 120                 125

Lys Thr His Val Asp Val Ala Phe Trp Gly Gly Val Ile Pro Gly Asn
    130                 135                 140

Ala His Glu Leu Leu Pro Leu Ile Asn Ala Gly Val Arg Gly Phe Lys
145                 150                 155                 160

Cys Phe Thr Ser Glu Ser Gly Val Asp Glu Phe Pro Gln Val Thr Lys
```

```
                       165                 170                 175
Asn Asp Leu Glu Met Ala Leu Lys Glu Leu Gln Lys Ala Asn Ser Val
            180                 185                 190

Leu Leu Tyr His Ala Glu Leu Pro Ala Pro Gln Glu Asn Val Thr Ser
            195                 200                 205

Asn Glu Thr Glu Lys Tyr Met Thr Tyr Leu Lys Thr Arg Pro Pro Ser
            210                 215                 220

Met Glu Val Asn Ala Ile Asp Met Ile Ile Asp Leu Thr Lys Lys Tyr
225                 230                 235                 240

Lys Val Arg Ser His Ile Val His Leu Ser Ala Ala Gly Ala Leu Pro
            245                 250                 255

Gln Leu Lys Lys Ala Arg Ser Glu Asn Val Pro Leu Ser Ile Glu Thr
            260                 265                 270

Cys His His Tyr Leu Thr Phe Ala Ala Glu Asp Val Pro Asp Gly His
            275                 280                 285

Thr Glu Tyr Lys Cys Ala Pro Pro Ile Arg Glu Glu Ser Asn Gln Glu
            290                 295                 300

Lys Leu Trp Gln Ala Leu Glu Asn Arg Asp Ile Asp Met Val Val Ser
305                 310                 315                 320

Asp His Ser Pro Ser Pro Ala Ala Leu Lys Gly Leu Cys Asn Gly Cys
            325                 330                 335

His Pro Asp Phe Leu Lys Ala Trp Gly Gly Ile Ala Gly Met Gln Phe
            340                 345                 350

Gly Leu Ser Leu Ile Arg Thr Gly Ala Ser Lys Arg Gly Phe Lys Ala
            355                 360                 365

His Asp Val Ser Arg Leu Leu Ser Ala Gly Pro Ala Lys Leu Thr Gly
            370                 375                 380

Leu Asp Gly Ile Lys Gly Gln Ile Lys Glu Gly Leu Asp Ala Asp Leu
385                 390                 395                 400

Val Ile Trp Asp Pro Glu Glu Glu Phe Lys Val Thr Lys Asp Ile Ile
            405                 410                 415

Gln His Lys Asn Lys Glu Thr Pro Tyr Leu Gly Met Thr Leu Lys Gly
            420                 425                 430

Lys Val His Ala Thr Val Val Arg Gly Asp Phe Val Tyr Arg Asn Gly
            435                 440                 445

Gln Pro Phe Glu Ile Pro Lys Gly Asn Leu Leu Ile Glu
450                 455                 460

<210> SEQ ID NO 8
<211> LENGTH: 1383
<212> TYPE: DNA
<213> ORGANISM: Ctenocephalides felis

<400> SEQUENCE: 8
ttcaataagt aaatttcctt ttggaatttc gaatggttgt ccattacggt aaacaaagtc      60
tcctcgtaca acagttgcat gaactttgcc cttcaacgtc attcctaagt atggtgtttc     120
tttattcttg tgttggatta tgtctttagt gaccttaaat tcttcctcag gatcccaaat     180
tactaaatca gcatccaagc cttctttgat ttgtcctttt atgccatcca gtccagttaa     240
tttcgcaggt cccgcagata taaacgaga tacatcatga gctttaaagc ctcttttaga     300
agcaccggtc cttattaaag ataatccaaa ctgcatacca gcaattccac cccaagcttt     360
taggaaatca ggatgacaac cattgcacag gcctttcagt gcagcaggtg atggagaatg     420
atcactgact accatatcaa tatctctgtt ttccaaagct tgccataatt tttcttgatt     480
```

-continued

```
actttcttct ctaattggtg gagcgcattt gtattcagta tgtccatctg gaacatcttc        540
agcagcaaag gttaagtaat gatgacaagt ttcaatcgaa agtggaacgt tctctgagcg        600 cgctttttc aattgcggta aagcacctgc tgctgataga tgcactatgt gagacctaac         660
tttatatttt tttgtgaggt ctataatcat atcaatagca tttacttcca tacttggagg        720
tcgtgttttc aggtaagtca tgtacttttc agtttcattg cttgtaacat tttcttgagg        780
agcgggtaat tcggcatggt acagaagtac ggaatttgct ttctggagct cttttagagc        840
catttccaga tcatttttag taacctgtgg aaactcatcg acaccacttt cacttgtaaa        900
acatttgaat cctcttactc cggcgttgat aagtggcaac aattcgtgcg cattgccagg        960
aatcacgcct ccccagaaag cgacatcaac atgcgtttta ccacaggctg aattcacttt       1020
tgttctcaaa ttctctacag tagttgtagg tgggatggaa ttcaaaggca tgtctactat       1080
tgtggtaatc ccgccccaag ctgctgcttt agtagctgtg gtgtatcctt cccaggattc       1140
tcttcctggt tcgttgacgt gcacatgaga gtctatcaca cctggccata ttgaaaattg       1200
accgtagtcc aacacctcaa ctttagtttc gttagctatc cttccactt cttctcctga        1260 aattatactt tttattcttc cggaggaatc aactacaatg ccagcatctc tttcagtacc       1320
atcaccgaga agaactcttc ggctacggaa tatcttcatt ggaggcgcgt tgttggtgca       1380
cgc                                                                     1383
```

<210> SEQ ID NO 9
<211> LENGTH: 1123
<212> TYPE: DNA
<213> ORGANISM: Ctenocephalides felis
<220> FEATURE:
<221> NAME/KEY: CDS
<222> LOCATION: (2)..(1123)

<400> SEQUENCE: 9

```
t atg ctg aat tgc aag aac ctt gtt aat gct gcg tgc acc aac aac gcg         49
  Met Leu Asn Cys Lys Asn Leu Val Asn Ala Ala Cys Thr Asn Asn Ala
    1               5                  10                  15 cct cca atg aag ata ttc cgt agc cga aga gtt ctt ctc ggt gat ggt           97
Pro Pro Met Lys Ile Phe Arg Ser Arg Arg Val Leu Leu Gly Asp Gly
            20                  25                  30 act gaa aga gat gct ggc att gta gtt gat tcc tcc gga aga ata aaa          145
Thr Glu Arg Asp Ala Gly Ile Val Val Asp Ser Ser Gly Arg Ile Lys
        35                  40                  45 agt ata att tca gga gaa gaa gtg gaa agg ata gct aac gaa act aaa          193
Ser Ile Ile Ser Gly Glu Glu Val Glu Arg Ile Ala Asn Glu Thr Lys
    50                  55                  60 gtt gag gtg ttg gac tac ggt caa ttt tca ata tgg cca ggt gtg ata          241
Val Glu Val Leu Asp Tyr Gly Gln Phe Ser Ile Trp Pro Gly Val Ile
65                  70                  75                  80 gac tct cat gtg cac gtc aac gaa cca gga aga gaa tcc tgg gaa gga          289
Asp Ser His Val His Val Asn Glu Pro Gly Arg Glu Ser Trp Glu Gly
                85                  90                  95 tac acc aca gct act aaa gca gca gct tgg ggc ggg att acc aca ata          337
Tyr Thr Thr Ala Thr Lys Ala Ala Ala Trp Gly Gly Ile Thr Thr Ile
            100                 105                 110 gta gac atg cct ttg aat tcc atc cca cct aca act act gta gag aat          385
Val Asp Met Pro Leu Asn Ser Ile Pro Pro Thr Thr Thr Val Glu Asn
        115                 120                 125 ttg aga aca aaa gtg aat tca gcc tgt ggt aaa acg cat gtt gat gtc          433
Leu Arg Thr Lys Val Asn Ser Ala Cys Gly Lys Thr His Val Asp Val
    130                 135                 140
```

```
gct ttc tgg gga ggc gtg att cct ggc aat gcg cac gaa ttg ttg cca        481
Ala Phe Trp Gly Gly Val Ile Pro Gly Asn Ala His Glu Leu Leu Pro
145                 150                 155                 160 ctt atc aac gcc gga gta aga gga ttc aaa tgt ttt aca agt gaa agt        529
Leu Ile Asn Ala Gly Val Arg Gly Phe Lys Cys Phe Thr Ser Glu Ser
                165                 170                 175 ggt gtc gat gag ttt cca cag gtt act aaa aat gat ctg gaa atg gct        577
Gly Val Asp Glu Phe Pro Gln Val Thr Lys Asn Asp Leu Glu Met Ala
            180                 185                 190 cta aaa gag ctc cag aaa gca aat tcc gta ctt ctg tac cat gcc gaa        625
Leu Lys Glu Leu Gln Lys Ala Asn Ser Val Leu Leu Tyr His Ala Glu
        195                 200                 205 tta ccc gct cct caa gaa aat gtt aca agc aat gaa act gaa aag tac        673
Leu Pro Ala Pro Gln Glu Asn Val Thr Ser Asn Glu Thr Glu Lys Tyr
    210                 215                 220 atg act tac ctg aaa aca cga cct cca agt atg gaa gta aat gct att        721
Met Thr Tyr Leu Lys Thr Arg Pro Pro Ser Met Glu Val Asn Ala Ile
225                 230                 235                 240 gat atg att ata gac ctc aca aaa aaa tat aaa gtt agg tct cac ata        769
Asp Met Ile Ile Asp Leu Thr Lys Lys Tyr Lys Val Arg Ser His Ile
                245                 250                 255 gtg cat cta tca gca gca ggt gct tta ccg caa ttg aaa aaa gcg cgc        817
Val His Leu Ser Ala Ala Gly Ala Leu Pro Gln Leu Lys Lys Ala Arg
            260                 265                 270 tca gag aac gtt cca ctt tcg att gaa act tgt cat cat tac tta acc        865
Ser Glu Asn Val Pro Leu Ser Ile Glu Thr Cys His His Tyr Leu Thr
        275                 280                 285 ttt gct gct gaa gat gtt cca gat gga cat act gaa tac aaa tgc gct        913
Phe Ala Ala Glu Asp Val Pro Asp Gly His Thr Glu Tyr Lys Cys Ala
    290                 295                 300 cca cca att aga gaa gaa agt aat caa gaa aaa tta tgg caa gct ttg        961
Pro Pro Ile Arg Glu Glu Ser Asn Gln Glu Lys Leu Trp Gln Ala Leu
305                 310                 315                 320 gaa aac aga gat att gat atg gta gtc agt gat cat tct cca tca cct       1009
Glu Asn Arg Asp Ile Asp Met Val Val Ser Asp His Ser Pro Ser Pro
                325                 330                 335 gct gca ctg aaa ggc ctg tgc aat ggt tgt cat cct gat ttc cta aaa       1057
Ala Ala Leu Lys Gly Leu Cys Asn Gly Cys His Pro Asp Phe Leu Lys
            340                 345                 350 gct tgg ggt gga att gct ggt atg cag ttt gga tta tct tta ata agg       1105
Ala Trp Gly Gly Ile Ala Gly Met Gln Phe Gly Leu Ser Leu Ile Arg
        355                 360                 365 acc ggt gct tct aaa aga                                                1123
Thr Gly Ala Ser Lys Arg
    370

<210> SEQ ID NO 10
<211> LENGTH: 374
<212> TYPE: PRT
<213> ORGANISM: Ctenocephalides felis

<400> SEQUENCE: 10

Met Leu Asn Cys Lys Asn Leu Val Asn Ala Ala Cys Thr Asn Asn Ala
 1               5                  10                  15

Pro Pro Met Lys Ile Phe Arg Ser Arg Val Leu Leu Gly Asp Gly
             20                  25                  30

Thr Glu Arg Asp Ala Gly Ile Val Val Asp Ser Ser Gly Arg Ile Lys
         35                  40                  45

Ser Ile Ile Ser Gly Glu Glu Val Glu Arg Ile Ala Asn Glu Thr Lys
```

| | 50 | | | | 55 | | | | 60 | | |
|---|---|---|---|---|---|---|---|---|---|---|---|
Val | Glu | Val | Leu | Asp | Tyr | Gly | Gln | Phe | Ser | Ile | Trp | Pro | Gly | Val | Ile
65 | | | | | 70 | | | | 75 | | | | | | 80

Asp Ser His Val His Val Asn Glu Pro Gly Arg Glu Ser Trp Glu Gly
          85                    90                    95

Tyr Thr Thr Ala Thr Lys Ala Ala Trp Gly Gly Ile Thr Thr Ile
              100                 105                 110

Val Asp Met Pro Leu Asn Ser Ile Pro Pro Thr Thr Val Glu Asn
          115                 120             125

Leu Arg Thr Lys Val Asn Ser Ala Cys Gly Lys Thr His Val Asp Val
130                 135                 140

Ala Phe Trp Gly Gly Val Ile Pro Gly Asn Ala His Glu Leu Leu Pro
145             150                 155                 160

Leu Ile Asn Ala Gly Val Arg Gly Phe Lys Cys Phe Thr Ser Glu Ser
              165                 170                 175

Gly Val Asp Glu Phe Pro Gln Val Thr Lys Asn Asp Leu Glu Met Ala
              180                 185                 190

Leu Lys Glu Leu Gln Lys Ala Asn Ser Val Leu Leu Tyr His Ala Glu
        195                 200                 205

Leu Pro Ala Pro Gln Glu Asn Val Thr Ser Asn Glu Thr Glu Lys Tyr
        210                 215                 220

Met Thr Tyr Leu Lys Thr Arg Pro Pro Ser Met Glu Val Asn Ala Ile
225                 230                 235                 240

Asp Met Ile Ile Asp Leu Thr Lys Lys Tyr Lys Val Arg Ser His Ile
              245                 250                 255

Val His Leu Ser Ala Ala Gly Ala Leu Pro Gln Leu Lys Lys Ala Arg
              260                 265                 270

Ser Glu Asn Val Pro Leu Ser Ile Glu Thr Cys His His Tyr Leu Thr
        275                 280                 285

Phe Ala Ala Glu Asp Val Pro Asp Gly His Thr Glu Tyr Lys Cys Ala
290                 295                 300

Pro Pro Ile Arg Glu Glu Ser Asn Gln Glu Lys Leu Trp Gln Ala Leu
305                 310                 315                 320

Glu Asn Arg Asp Ile Asp Met Val Val Ser Asp His Ser Pro Ser Pro
              325                 330                 335

Ala Ala Leu Lys Gly Leu Cys Asn Gly Cys His Pro Asp Phe Leu Lys
              340                 345                 350

Ala Trp Gly Gly Ile Ala Gly Met Gln Phe Gly Leu Ser Leu Ile Arg
              355                 360                 365

Thr Gly Ala Ser Lys Arg
        370

<210> SEQ ID NO 11
<211> LENGTH: 1123
<212> TYPE: DNA
<213> ORGANISM: Ctenocephalides felis

<400> SEQUENCE: 11
tcttttagaa gcaccggtcc ttattaaaga taatccaaac tgcataccag caattccacc      60
ccaagctttt aggaaatcag gatgacaacc attgcacagg cctttcagtg cagcaggtga     120
tggagaatga tcactgacta ccatatcaat atctctgttt ccaaagcttt gccataattt     180
ttcttgatta ctttcttctc taattggtgg agcgcatttg tattcagtat gtccatctgg     240
aacatcttca gcagcaaagg ttaagtaatg atgacaagtt tcaatcgaaa gtggaacgtt     300

```
ctctgagcgc gcttttttca attgcggtaa agcacctgct gctgatagat gcactatgtg      360
agacctaact ttatatttt ttgtgaggtc tataatcata tcaatagcat ttacttccat       420
acttggaggt cgtgttttca ggtaagtcat gtacttttca gtttcattgc ttgtaacatt      480
ttcttgagga gcgggtaatt cggcatggta cagaagtacg gaatttgctt tctggagctc      540
ttttagagcc atttccagat cattttagt aacctgtgga aactcatcga caccactttc      600
acttgtaaaa catttgaatc ctcttactcc ggcgttgata agtggcaaca attcgtgcgc      660
attgccagga atcacgcctc cccagaaagc gacatcaaca tgcgttttac cacaggctga     720
attcactttt gttctcaaat tctctacagt agttgtaggt gggatggaat tcaaaggcat     780
gtctactatt gtggtaatcc cgccccaagc tgctgcttta gtagctgtgg tgtatccttc     840
ccaggattct cttcctggtt cgttgacgtg cacatgagag tctatcacac ctggccatat    900
tgaaaattga ccgtagtcca acacctcaac tttagtttcg ttagctatcc tttccacttc    960
ttctcctgaa attatacttt ttattcttcc ggaggaatca actacaatgc cagcatctct   1020
ttcagtacca tcaccgagaa gaactcttcg gctacggaat atcttcattg gaggcgcgtt   1080
gttggtgcac gcagcattaa caaggttctt gcaattcagc ata                     1123

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
catgccatgg cgtgcaccaa caacgcgcct cc                                   32

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
gcggtacctc attcaataag taaatttcct tttgg                                35

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
gcggatccta tgctgaattg caagaacctt g                                    31

<210> SEQ ID NO 15
<211> LENGTH: 30
<212> TYPE: DNA
<213> ORGANISM: Artificial Sequence
<220> FEATURE:
```

```
-continued

<223> OTHER INFORMATION: Description of Artificial Sequence:  Synthetic
      Primer

<400> SEQUENCE: 15
caggtaccct cttttagaag caccggtccc                                            30
```

US 6,905,682 B2

FLEA ALLANTOINASE PROTEINS AND USES THEREOF

CROSS REFERENCE TO RELATED APPLICATIONS

This application is a divisional of U.S. patent application Ser. No. 09/894,698, filed Jun. 28, 2001 now U.S. Pat. No. 6,469,152, entitled FLEA ALLANTOINASE NUCLEIC ACID MOLECULES AND USES THEREOF, which is a continuation-in-part of U.S. patent application Ser. No. 09/543,668, filed Apr. 7, 2000 now abandoned entitled "FLEA ALLANTOINASE NUCLEIC ACID MOLECULES, PROTEINS AND USES THEREOF, now abandoned, and claims priority to U.S. Provisional Patent Application Ser. No. 60/128,704, filed Apr. 9, 1999 entitled "NOVEL FLEA HEAD, NERVE CORD, HINDGUT AND MALPIGHIAN TUBULE NUCLEIC ACID MOLECULES, PROTEINS AND USES THEREOF".

FIELD OF THE INVENTION

The present invention relates to flea allantoinase nucleic acid molecules, proteins encoded by such nucleic acid molecules, antibodies raised against such proteins, inhibitors of such proteins and methods to detect such inhibitors. The present invention also includes therapeutic compositions comprising such nucleic acid molecules, proteins, antibodies, and/or other inhibitors, as well as uses thereof.

BACKGROUND OF THE INVENTION

Flea infestation of animals is a health and economic concern because fleas are known to cause and/or transmit a variety of diseases. Fleas directly cause a variety of diseases, including allergies, and also carry a variety of infectious agents including, but not limited to, endoparasites (e.g., nematodes, cestodes, trematodes and protozoa), bacteria and viruses. In particular, the bites of fleas are a problem for animals maintained as pets because the infestation becomes a source of annoyance not only for the pet but also for the pet owner who may find his or her home generally contaminated with insects. As such, fleas are a problem not only when they are on an animal but also when they are in the general environment of the animal.

Bites from fleas are a particular problem because they not only can lead to disease transmission but also can cause a hypersensitive response in animals which is manifested as disease. For example, bites from fleas can cause an allergic disease called flea allergic (or allergy) dermatitis (FAD). A hypersensitive response in animals typically results in localized tissue inflammation and damage, causing substantial discomfort to the animal.

The medical importance of flea infestation has prompted the development of reagents capable of controlling flea infestation. Commonly encountered methods to control flea infestation are generally focused on use of insecticides. While some of these to products are efficacious, most, at best, offer protection of a very limited duration. Furthermore, many of the methods are often not successful in reducing flea populations. In particular, insecticides have been used to prevent flea infestation of animals by adding such insecticides to shampoos, powders, collars, sprays, spot-on formulations foggers and liquid bath treatments (i.e., dips). Reduction of flea infestation on the pet has been unsuccessful for one or more of the following reasons: failure of owner compliance (frequent administration is required); behavioral or physiological intolerance of the pet to the pesticide product or means of administration; and the emergence of flea populations resistant to the prescribed dose of pesticide.

Allantoinase is involved in the catalysis of the reaction converting allantoin to allantoic acid. This is a middle step in purine catabolism, which in insects results in the secretion of urea as the end product. The enzyme is located in the peroxisomes of the liver and kidney in amphibians. There is no known mammalian homologue to allantoinase, as mammals secrete uric acid, a precursor to allantoin. As such, flea allantoinase represents a novel target for anti-flea vaccines and chemotherapeutic drugs. Therefore, isolation and sequencing of flea allantoinase genes may be critical for use in identifying specific agents for treating animals for flea infestation.

SUMMARY OF THE INVENTION

The present invention relates to a novel product and process for protection of animals from flea infestation.

The present invention provides flea allantoinase proteins; nucleic acid molecules encoding flea allantoinase proteins; antibodies raised against such proteins; mimetopes of such proteins or antibodies; and compounds that inhibit flea allantoinase activity (i.e, inhibitory compounds or inhibitors).

The present invention also includes methods to obtain such proteins, mimetopes, nucleic acid molecules, antibodies and inhibitory compounds. The present invention also includes the use of proteins and antibodies to identify such inhibitory compounds as well as assay kits to identify such inhibitory compounds. Also included in the present invention are therapeutic compositions comprising proteins, mimetopes, nucleic acid molecules, antibodies and inhibitory compounds of the present invention including protective compounds derived from a protein of the present invention that inhibit the activity of allantoinase proteins; also included are uses of such therapeutic compounds to reduce flea infestation.

One embodiment of the present invention is an isolated nucleic acid molecule that hybridizes with a nucleic acid sequence having SEQ ID NO:1, SEQ ID NO:3, SEQ ID NO:4, SEQ ID NO:5, SEQ ID NO:6, SEQ ID NO:8, SEQ ID NO:9, and SEQ ID NO:11 under conditions that allow less than or equal to about 30% base pair mismatch.

Another embodiment of the present invention is an isolated nucleic acid molecule having nucleic acid sequence that is at least about 70% identical to SEQ ID NO:1, SEQ ID NO:3, SEQ ID NO:4, SEQ ID NO:5, SEQ ID NO:6, SEQ ID NO:8, SEQ ID NO:9, and SEQ ID NO:11.

The present invention also relates to recombinant molecules, recombinant viruses and recombinant cells that include a nucleic acid molecule of the present invention. Also included are methods to produce such nucleic acid molecules, recombinant molecules, recombinant viruses and recombinant cells.

Another embodiment of the present invention includes an isolated protein that is at least about 70% identical to an amino acid sequence selected from the group consisting of SEQ ID NO:2, SEQ ID NO:7 and SEQ ID NO:10 and fragments thereof, wherein such fragments can elicit an immune response against respective flea proteins or have activity comparable to respective flea proteins.

Another embodiment of the present invention includes an isolated protein encoded by a nucleic acid molecule that hybridizes with the complement of a nucleic acid sequence having SEQ ID NO:1, SEQ ID NO:4, SEQ ID NO:6 and SEQ ID NO:9, under conditions that allow less than or equal to about 30% base pair mismatch.

DETAILED DESCRIPTION OF THE INVENTION

The present invention provides for flea allantoinase nucleic acid molecules, proteins encoded by such nucleic acid molecules, antibodies raised against such proteins, and inhibitors of such proteins. As used herein, flea allantoinase nucleic acid molecules and proteins encoded by such nucleic acid molecules are also referred to as allantoinase nucleic acid molecules and proteins. Flea allantoinase nucleic acid molecules and proteins of the present invention can be isolated from a flea or prepared recombinantly or synthetically. Flea allantoinase nucleic acid molecules of the present invention can be RNA or DNA, or modified forms thereof, and can be double-stranded or single-stranded; examples of nucleic acid molecules include, but are not limited to, complementary DNA (cDNA) molecules, genomic DNA molecules, synthetic DNA molecules, DNA molecules which are specific tags for messenger RNA, and corresponding mRNA molecules. As such, a flea nucleic acid molecule of the present invention is not intended refer to an entire chromosome within which such a nucleic acid molecule is contained, however, a flea allantoinase cDNA of the present invention may include all regions such as regulatory regions that control production of flea allantoinase proteins encoded by such a cDNA (such as, but not limited to, transcription, translation or post-translation control regions) as well as the coding region itself, and any introns or non-translated coding regions. As used herein, the phrase "flea allantoinase protein" refers to a protein encoded by a flea allantoinase nucleic acid molecule.

Flea allantoinase nucleic acid molecules of known length isolated from a flea, such as *Ctenocephalides felis* are denoted "nCfALN$_\#$", for example nCfALN$_{2035}$, wherein "#" refers to the number of nucleotides in that molecule, and flea allantoinase proteins of known length are denoted "PCfALN$_\#$" (for example PCfALN$_{483}$) wherein "#" refers to the number of amino acid residues in that molecule.

The present invention also provides for flea allantoinase DNA molecules that are specific tags for messenger RNA molecules. Such DNA molecules can correspond to an entire or partial sequence of a messenger RNA, and therefore, a DNA molecule corresponding to such a messenger RNA molecule (i.e. a cDNA molecule), can encode a full-length or partial-length protein. A nucleic acid molecule encoding a partial-length protein can be used directly as a probe or indirectly to generate primers to identify and/or isolate a cDNA nucleic acid molecule encoding a corresponding, or structurally related, full-length protein. Such a partial cDNA nucleic acid molecule can also be used in a similar manner to identify a genomic nucleic acid molecule, such as a nucleic acid molecule that contains the complete gene including regulatory regions, exons and introns. Methods for using partial flea allantoinase cDNA molecules and sequences to isolate full-length and corresponding cDNA molecules are described in the examples herein below.

The proteins and nucleic acid molecules of the present invention can be obtained from their natural source, or can be produced using, for example, recombinant nucleic acid technology or chemical synthesis. Also included in the present invention is the use of these proteins and nucleic acid molecules as well as antibodies and inhibitory compounds thereto as therapeutic compositions to protect animals from flea infestation, as well as in other applications, such as those disclosed below.

One embodiment of the present invention is an isolated protein that includes a flea allantoinase protein. It is to be noted that the term "a" or "an" entity refers to one or more of that entity; for example, a protein, a nucleic acid molecule, an antibody and a therapeutic composition refers to "one or more" or "at least one" protein, nucleic acid molecule, antibody and therapeutic composition respectively. As such, the terms "a" (or "an"), "one or more" and "at least one" can be used interchangeably herein. It is also to be noted that the terms "comprising", "including", and "having" can be used interchangeably. According to the present invention, an isolated, or biologically pure, flea allantoinase protein, is a protein that has been removed from its natural milieu, such as a flea protein extract having allantoinase activity. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

As used herein, isolated flea allantoinase proteins of the present invention can be full-length proteins or any homologue of such proteins. An isolated protein of the present invention, including a homologue, can be identified in a straight-forward manner by the protein's ability to elicit an immune response against a flea allantoinase protein or by the protein's ability to exhibit flea allantoinase activity. Examples of flea allantoinase homologue proteins include flea allantoinase proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homologue includes at least one epitope capable of eliciting an immune response against a flea allantoinase protein, and/or of binding to an antibody directed against a flea allantoinase protein. That is, when the homologue is administered to an animal as an immunogen, using techniques known to those skilled in the art, the animal will produce an immune response against at least one epitope of a natural flea allantoinase protein. The ability of a protein to effect an immune response can be measured using techniques known to those skilled in the art. As used herein, the term "epitope" refers to the smallest portion of a protein or other antigen capable of selectively binding to the antigen binding site of an antibody or a T cell receptor. It is well accepted by those skilled in the art that the minimal size of a protein epitope is about four to six amino acids. As is appreciated by those skilled in the art, an epitope can include amino acids that naturally are contiguous to each other as well as amino acids that, due to the tertiary structure of the natural protein, are in sufficiently close proximity to form an epitope. According to the present invention, an epitope includes a portion of a protein comprising at least 4 amino acids, at least 5 amino acids, at least 6 amino acids, at least 10 amino acids, at least 15 amino acids, at least 20 amino acids, at least 25 amino acids, at least 30 amino acids, at least 35 amino acids, at least 40 amino acids or at least 50 amino acids in length.

In one embodiment of the present invention a flea allantoinase homologue protein has flea allantoinase activity, i.e. the homologue exhibits an activity similar to its natural counterpart. Methods to detect and measure such activities are known to those skilled in the art.

Flea allantoinase homologue proteins can be the result of natural allelic variation or natural mutation. Flea allantoinase protein homologues of the present invention can also be produced using techniques known in the art including, but not limited to, direct modifications to the protein or modifications to the gene encoding the protein using, for example, classic or recombinant DNA techniques to effect random or targeted mutagenesis.

Flea allantoinase proteins of the present invention are encoded by flea allantoinase nucleic acid molecules. As used herein, flea allantoinase nucleic acid molecules include nucleic acid sequences related to natural flea allantoinase genes, and, preferably, to C. felis flea allantoinase genes. As used herein, flea allantoinase genes include all regions such as regulatory regions that control production of flea allantoinase proteins encoded by such genes (such as, but not limited to, transcription, translation or post-translation control regions) as well as the coding region itself, and any introns or non-translated coding regions. As used herein, a nucleic acid molecule that "includes" or "comprises" a sequence may include that sequence in one contiguous array, or may include the sequence as fragmented exons such as is often found for a flea gene. As used herein, the term "coding region" refers to a continuous linear array of nucleotides that translates into a protein. A full-length coding region is that coding region that is translated into a full-length, i.e., a complete protein as would be initially translated in its natural millieu, prior to any post-translational modifications.

One embodiment of the present invention is a C. felis flea allantoinase gene that includes the nucleic acid sequence SEQ ID NO:1, SEQ ID NO:3, SEQ ID NO:4, SEQ ID NO:5, SEQ ID NO:6, SEQ ID NO:8, SEQ ID NO:9, and SEQ ID NO:11. These nucleic acid sequences are further described herein. For example, nucleic acid sequence SEQ ID NO:1 represents the deduced sequence of the coding strand of a C. felis cDNA denoted herein as C. felis allantoinase nucleic acid molecule $nCfALN_{2035}$, the production of which is disclosed in the Examples. Nucleic acid molecule SEQ ID NO:1 comprises an apparently full-length coding region. The complement of SEQ ID NO:1 (represented herein by SEQ ID NO:3) refers to the nucleic acid sequence of the strand fully complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is fully complementary to (i.e., can form a complete double helix with) the strand for which the sequence is cited. It should be noted that since nucleic acid sequencing technology is not entirely error-free, SEQ ID NO:1 (as well as other nucleic acid and protein sequences presented herein) represents an apparent nucleic acid sequence of the nucleic acid molecule encoding a flea allantoinase protein of the present invention.

Translation of SEQ ID NO:1, the coding strand of $nCfALN_{2035}$, as well as translation of SEQ ID NO:4, the coding strand of $nCfALN_{1449}$, which represents the coding region of SEQ ID NO:1, each yields a protein of about 483 amino acids, denoted herein as $PCfALN_{483}$, the amino acid sequence of which is presented in SEQ ID NO:2, assuming a first in-frame codon extending from nucleotide 1 to nucleotide 3 of SEQ ID NO:4.

In one embodiment, a gene or other nucleic acid molecule of the present invention can be an allelic variant that includes a similar but not identical sequence to SEQ ID NO:1, SEQ ID NO:3, SEQ ID NO:4, SEQ ID NO:5, SEQ ID NO:6, SEQ ID NO:8, SEQ ID NO:9, and SEQ ID NO:11. For example, an allelic variant of a C. felis allantoinase gene including SEQ ID NO:1, SEQ ID NO:3, SEQ ID NO:4, SEQ ID NO:5, SEQ ID NO:6, SEQ ID NO:8, SEQ ID NO:9, and SEQ ID NO:11 is a gene that occurs at essentially the same locus (or loci) in the genome as the gene including SEQ ID NO:1, SEQ ID NO:3, SEQ ID NO:4, SEQ ID NO:5, SEQ ID NO:6, SEQ ID NO:8, SEQ ID NO:9, and SEQ ID NO:11, but which, due to natural variations caused by, for example, mutation or recombination, has a similar but not identical sequence. Because natural selection typically selects against alterations that affect function, allelic variants (i.e. alleles corresponding to, or of, cited nucleic acid sequences) usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to occur naturally within a given flea species, since the genome is diploid, and sexual reproduction will result in the reassortment of alleles.

In one embodiment of the present invention, isolated flea allantoinase proteins are encoded by nucleic acid molecules that hybridize under stringent hybridization conditions to genes or other nucleic acid molecules encoding flea allantoinase proteins, respectively. The minimal size of flea allantoinase proteins of the present invention is a size sufficient to be encoded by a nucleic acid molecule capable of forming a stable hybrid (i.e., hybridizing under stringent hybridization conditions) with the complementary sequence of a nucleic acid molecule encoding the corresponding natural protein. The size of a nucleic acid molecule encoding such a protein is dependent on the nucleic acid composition and the percent homology between the flea allantoinase nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered (i.e., localized) in distinct regions on a given nucleic acid molecule.

The minimal size of a nucleic acid molecule capable of forming a stable hybrid with a gene encoding a flea allantoinase protein is at least about 12 to about 15 nucleotides in length if the nucleic acid molecule is GC-rich and at least about 15 to about 17 bases in length if it is AT-rich. The minimal size of a nucleic acid molecule used to encode a flea allantoinase protein homologue of the present invention is from about 12 to about 18 nucleotides in length. Thus, the minimal size of flea allantoinase protein homologues of the present invention is from about 4 to about 6 amino acids in length. There is no limit, other than a practical limit, on the maximal size of a nucleic acid molecule encoding a flea allantoinase protein of the present invention because a nucleic acid molecule of the present invention can include a portion of a gene or cDNA or RNA, an entire gene or cDNA or RNA, or multiple genes or cDNA or RNA. The preferred size of a protein encoded by a nucleic acid molecule of the present invention depends on whether a full-length, fusion, multivalent, or functional portion of such a protein is desired.

Stringent hybridization conditions are determined based on defined physical properties of the flea allantoinase nucleic acid molecule to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267–284, each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m = 81.5° \text{ C.} + 16.6 \log M + 0.41(\% \; G+C) - 500/n - 0.61(\% \text{ formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d = 4(G+C) + 2(A+T).$$

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions (by altering, for example, the salt concentration, the concentration of helix destabilizing agents, or the temperature) so that only nucleic acid hybrids with greater than a specified % base pair mismatch will hybridize. Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under conditions that would allow less than or equal to 30% pair mismatch with a flea allantoinase nucleic acid molecule of about 150 bp in length or greater, the following conditions could preferably be used. The average G+C content of flea DNA is about 37%, as calculated from known flea nucleic acid sequences. The unknown nucleic acid molecules would be attached to a support membrane, and the 150 bp probe would be labeled, e.g. with a radioactive tag. The hybridization reaction could be carried out in a solution comprising 2×SSC in the absence of nucleic acid helix destabilizing compounds, at a temperature of about 37° C. (low stringency conditions). Solutions of differing concentrations of SSC can be made by one of skill in the art by diluting a stock solution of 20×SSC (175.3 gram NaCl and about 88.2 gram sodium citrate in 1 liter of water, pH 7) to obtain the desired concentration of SSC. The skilled artisan would calculate the washing conditions required to allow up to 30% base pair mismatch. For example, in a wash solution comprising 1×SSC in the absence of nucleic acid helix destabilizing compounds, the $T_m$ of perfect hybrids would be about 77° C.:

$$81.5° \text{ C.} + 16.6 \log (0.15 \text{ M}) + (0.41 \times 73) - (500/150) - (0.61 \times 0) = 77.5° \text{ C.}$$

Thus, to achieve hybridization with nucleic acid molecules having about 30% base pair mismatch, hybridization washes would be carried out at a temperature of less than or equal to 47.5° C. It is thus within the skill of one in the art to calculate additional hybridization temperatures based on the desired percentage base pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base pair mismatch will not vary significantly from 47.5° C.

Furthermore, it is known in the art that there are commercially available computer programs for determining the degree of similarity between two nucleic acid or protein sequences. These computer programs include various known methods to determine the percentage identity and the number and length of gaps between hybrid nucleic acid molecules or proteins. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, the SeqLab® Wisconsin Package™ Version 10.0-UNIX sequence analysis software, available from Genetics Computer Group, Madison, Wis. (hereinafter "SeqLab"); and DNAsis® sequence analysis software, version 2.0, available from Hitachi Software, San Bruno, Calif. (hereinafter "DNAsis"). Such software programs represent a collection of algorithms paired with a graphical user interface for using the algorithms. The DNAsis and SeqLab software, for example, employ a particular algorithm, the Needleman-Wunsch algorithm to perform pair-wise comparisons between two sequences to yield a percentage identity score, see Needleman, S. B. and Wunsch, C. D., 1970, *J. Mol. Biol.*, 48, 443, which is incorporated herein by reference in its entirety. Such algorithms, including the Needleman-Wunsch algorithm, are commonly used by those skilled in the nucleic acid and amino acid sequencing art to compare sequences. A preferred method to determine percent identity among amino acid sequences and also among nucleic acid sequences includes using the Needleman-Wunsch algorithm, available in the SeqLab software, using the Pairwise Comparison/Gap function with the nwsgapdna.cmp scoring matrix, the gap creation penalty and the gap extension penalties set at default values, and the gap shift limits set at maximum (hereinafter referred to as "SeqLab default parameters"). An additional preferred method to determine percent identity among amino acid sequences and also among nucleic acid sequences includes using the Higgins-Sharp algorithm, available in the DNAsis software, with the gap penalty set at 5, the number of top diagonals set at 5, the fixed gap penalty set at 10, the k-tuple set at 2, the window size set at 5, and the floating gap penalty set at 10. A particularly preferred method to determine percent identity among amino acid sequences and also among nucleic acid sequences includes using the Needleman-Wunsch algorithm available in the SeqLab software, using the SeqLab default parameters.

One embodiment of the present invention includes a flea allantoinase protein. A preferred flea allantoinase protein includes a protein encoded by a nucleic acid molecule that hybridizes under conditions that preferably allow less than or equal to 30% base pair mismatch, preferably under conditions that allow less than or equal to 20% base pair mismatch, preferably under conditions that allow less than or equal to 10% base pair mismatch, preferably under conditions that allow less than or equal to 8% base pair mismatch, preferably under conditions that allow less than or equal to 5% base pair mismatch or preferably under conditions that allow less than or equal to 2% base pair mismatch with a nucleic acid molecule selected from the group consisting of SEQ ID NO:3, SEQ ID NO:5, SEQ ID NO:8 and SEQ ID NO:11.

Another embodiment of the present invention includes a flea allantoinase protein encoded by a nucleic acid molecule that hybridizes under conditions comprising, (a) all hybridizing in a solution comprising 1×SSC in the absence of nucleic acid helix destabilizing compounds, at a temperature of 37° C. and (b) washing in a solution comprising 1×SSC in the absence of nucleic acid helix destabilizing compounds, at a temperature of 47° C., to an isolated nucleic acid molecule selected from the group consisting of SEQ ID NO:3, SEQ ID NO:5, SEQ ID NO:8 and SEQ ID NO:11.

Another preferred flea allantoinase protein of the present invention includes a protein that is encoded by a nucleic acid molecule that is preferably at least 70% identical, preferably at least 80% identical, preferably at least 90% identical, preferably at least 92% identical, preferably at least 95% identical or preferably at least 98% identical to a nucleic acid molecule having the nucleic acid sequence SEQ ID NO:1, SEQ ID NO:4, SEQ ID NO:6 and SEQ ID NO:9; also preferred are fragments (i.e. portions) of such proteins encoded by nucleic acid molecules that are at least 30 nucleotides. Percent identity as used herein is determined using the Needleman-Wunsch algorithm, available in the SeqLab software using default parameters.

Additional preferred flea allantoinase proteins of the present invention include proteins having the amino acid sequence SEQ ID NO:2, SEQ ID NO:7 and SEQ ID NO:10, and proteins comprising homologues of a protein having the amino acid sequence SEQ ID NO:2, SEQ ID NO:7 and SEQ ID NO:10, wherein such a homologue comprises at least one epitope that elicits an immune response against a protein having an amino acid sequence SEQ ID NO:2, SEQ ID NO:7 and SEQ ID NO:10. Likewise, also preferred are proteins encoded by nucleic acid molecules comprising nucleic acid sequence SEQ ID NO:1, SEQ ID NO;4, SEQ ID NO:6 and SEQ ID NO:9, or by homologues thereof.

A preferred isolated flea allantoinase protein of the present invention is a protein encoded by at least one of the following nucleic acid molecules: $nCfALN_{2035}$, $nCfALN_{1449}$, $nCfALN_{1383}$, and $nCfALN_{1123}$, or allelic variants of any of these nucleic acid molecules. Also preferred is an isolated protein encoded by a nucleic acid molecule having nucleic acid sequence SEQ ID NO:1, SEQ ID NO:4, SEQ ID NO:6 and SEQ ID NO:9; or a protein encoded by an allelic variant of any of these listed nucleic acid molecules.

Preferred flea allantoinase proteins of the present invention include proteins having amino acid sequences that are at least 70%, preferably 80%, preferably 90%, preferably 92%, preferably 95%, preferably at least 98%, preferably at least 99%, or preferably 100% identical to amino acid sequence SEQ ID NO:2, SEQ ID NO:7 and SEQ ID NO:10 and proteins encoded by allelic variants of nucleic acid molecules encoding flea allantoinase proteins having amino acid sequences SEQ ID NO:2, SEQ ID NO:7 and SEQ ID NO:10. Also preferred are fragments thereof having at least 10 amino acid residues.

In one embodiment of the present invention, *C. felis* allantoinase proteins comprise amino acid sequence SEQ ID NO:2, SEQ ID NO:7 and SEQ ID NO:10 (including, but not limited to, the proteins consisting of amino acid sequence SEQ ID NO:2, SEQ ID NO:7 and SEQ ID NO:10, fusion proteins and multivalent proteins), and proteins encoded by allelic variants of nucleic acid molecules encoding proteins having amino acid sequence SEQ ID NO:2, SEQ ID NO:7 and SEQ ID NO:10.

In one embodiment, a preferred flea allantoinase protein comprises an amino acid sequence of at least 6 amino acids, preferably at least 10 amino acids, preferably at least 15 amino acids, preferably at least 20 amino acids, preferably at least 25 amino acids, preferably at least 30 amino acids, preferably at least 35 amino acids, preferably at least 40 amino acids, preferably at least 50 amino acids, preferably at least 75 amino acids, preferably at least 100 amino acids, preferably at least 125 amino acids, preferably at least 150 amino acids, preferably at least 175 amino acids, preferably at least 200 amino acids, preferably at least 250 amino acids, preferably at least 300 amino acids, preferably at least 350 amino acids, preferably at least 400 amino acids, preferably at least 450 amino acids, preferably at least 475 amino acids, or preferably at least 480 amino acids. In another embodiment, preferred flea allantoinase proteins comprise full-length proteins, i.e., proteins encoded by full-length coding regions, or post-translationally modified proteins thereof, such as mature proteins from which initiating methionine and/or signal sequences or "pro" sequences have been removed.

Additional preferred flea allantoinase proteins of the present invention include proteins encoded by nucleic acid molecules comprising at least a portion of $nCfALN_{2035}$, $nCfALN_{1449}$, $nCfALN_{1383}$, and $nCfALN_{1123}$, as well as flea allantoinase proteins encoded by allelic variants of such nucleic acid molecules. A portion of such flea allantoinase nucleic acid molecule is preferably at least 30 nucleotides in length.

Also preferred are flea allantoinase proteins encoded by nucleic acid molecules having nucleic acid sequences comprising at least a portion of SEQ ID NO:1, SEQ ID NO:4, SEQ ID NO:6 and SEQ ID NO:9, as well as allelic variants of these nucleic acid molecules. A portion of such flea allantoinase nucleic acid molecule is preferably at least 30 nucleotides in length.

In another embodiment, a preferred flea allantoinase protein of the present invention is encoded by a nucleic acid molecule comprising at least 20 nucleotides, preferably at least 25 nucleotides, preferably at least 30 nucleotides, preferably at least 40 nucleotides, preferably at least 50 nucleotides, preferably at least 75 nucleotides, preferably at least 100 nucleotides, preferably at least 200 nucleotides, preferably at least 400 nucleotides, preferably at least 500 nucleotides, preferably at least 750 nucleotides, preferably at least 1000 nucleotides, preferably at least 1500 nucleotides, preferably at least 1800 nucleotides, preferably at least 2000 nucleotides, or preferably at least 2035 nucleotides. Within this embodiment is a flea allantoinase protein encoded by at least a portion of $nCfALN_{2035}$, $nCfALN_{1449}$, $nCfALN_{1383}$, and $nCfALN_{1123}$, or by an allelic variant of any of these nucleic acid molecules. Preferred flea allantoinase proteins of the present invention are encoded by nucleic acid molecules comprising apparently full-length flea allantoinase coding region, i.e., nucleic acid molecules encoding an apparently full-length flea allantoinase protein.

Preferred flea allantoinase proteins of the present invention can be used to develop inhibitors that, when administered to an animal in an effective manner, are capable of protecting that animal from flea infestation. In accordance with the present invention, the ability of an inhibitor of the present invention to protect an animal from flea infestation refers to the ability of that protein to, for example, treat, ameliorate and/or prevent infestation caused by fleas. In particular, the phrase "to protect an animal from flea infestation" refers to reducing the potential for flea population expansion on and around the animal (i.e., reducing the flea burden). Preferably, the flea population size is decreased, optimally to an extent that the animal is no longer bothered by fleas. A host animal, as used herein, is an animal from which fleas can feed by attaching to and feeding through the skin of the animal. Fleas, and other ectoparasites, can live on a host animal for an extended period of time or can attach temporarily to an animal in order to feed. At any given time, a certain percentage of a flea population can be on a host animal whereas the remainder can be in the environment of the animal. Such an environment can include not only adult fleas, but also flea eggs and/or flea larvae. The environment can be of any size such that fleas in the environment are able to jump onto and off of a host animal. For example, the environment of an animal can include plants, such as crops, from which fleas infest an animal. As such, it is desirable not only to reduce the flea burden on an animal per se, but also to reduce the flea burden in the environment of the animal.

Suitable fleas to target include any flea that is essentially incapable of causing disease in an animal administered an inhibitor of the present invention. As such, fleas to target include any flea that produces a protein that can be targeted by an inhibitory compound that inhibits a flea allantoinase protein function, thereby resulting in the decreased ability of the parasite to cause disease in an animal. Preferred fleas to target include fleas of the following genera: *Ctenocephalides, Cyopsyllus, Diamanus (Oropsylla), Echidnophaga, Nosopsyllus, Pulex, Tunga,* and *Xenopsylla,* with those of the species *Ctenocephalides canis, Ctenocephalides felis, Diamanus montanus, Echidnophaga gallinacea, Nosopsyllus faciatus, Pulex irritans, Pulex simulans, Tunga penetrans* and *Xenopsylla cheopis* being more preferred, with *C. felis* being even more preferred. Such fleas are also preferred for the isolation of proteins or nucleic acid molecules of the present invention.

One embodiment of a flea allantoinase protein of the present invention is a fusion protein that includes a flea allantoinase protein-containing domain attached to one or more fusion segments. Suitable fusion segments for use with the present invention include, but are not limited to, segments that can: enhance a protein's stability; act as an immunopotentiator; and/or assist in purification of a flea allantoinase protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the flea allantoinase-containing domain of the protein and can be susceptible to cleavage in order to enable straight-forward recovery of a flea allantoinase protein. Fusion proteins are preferably produced by culturing a recombinant cell transformed with a fusion nucleic acid molecule that encodes a protein including the fusion segment attached to either the carboxyl and/or amino terminal end of a flea allantoinase-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

The present invention also includes mimetopes of flea allantoinase proteins of the present invention. As used herein, a mimetope of a flea allantoinase protein of the present invention refers to any compound that is able to mimic the activity of such a flea allantoinase protein, often because the mimetope has a structure that mimics the particular flea allantoinase protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention, Mimetopes can also be obtained by generating random samples of molecules, such as oligonucleotides, peptides or other organic molecules, and screening such samples by affinity chromatography techniques using the corresponding binding partner.

Another embodiment of the present invention is an isolated nucleic acid molecule comprising a flea allantoinase nucleic acid molecule, i.e. a nucleic acid molecule that can be isolated from a flea cDNA library. As used herein, flea allantoinase nucleic acid molecules has the same meaning as flea allantoinase nucleic acid molecule. The identifying characteristics of such nucleic acid molecules are heretofore described. A nucleic acid molecule of the present invention can include an isolated natural flea allantoinase gene or a homologue thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of a flea allantoinase nucleic acid molecule of the present invention is from about 12 to about 18 nucleotides in length.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. Isolated flea allantoinase nucleic acid molecules of the present invention, or homologues thereof, can be isolated from a natural source or produced using recombinant DNA technology (e.g., polymerase chain reaction (PCR) amplification or cloning) or chemical synthesis. Isolated flea allantoinase nucleic acid molecules, and homologues thereof, can include, for example, natural allelic variants and nucleic acid molecules modified by nucleotide insertions, deletions, substitutions, and/or inversions in a manner such that the modifications do not substantially interfere with the nucleic acid molecule's ability to encode a flea allantoinase protein of the present invention.

A flea allantoinase nucleic acid molecule homologue can be produced using a number of methods known to those skilled in the art, see, for example, Sambrook et al., ibid., which is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologues can be selected by hybridization with flea allantoinase nucleic acid molecules or by screening the function of a protein encoded by the nucleic acid molecule (e.g., ability to elicit an immune response against at least one epitope of a flea allantoinase protein or to effect flea allantoinase activity).

An isolated flea allantoinase nucleic acid molecule of the present invention can include a nucleic acid sequence that encodes at least one flea allantoinase protein of the present invention respectively, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a flea allantoinase protein.

A preferred nucleic acid molecule of the present invention, when administered to an animal, is capable of protecting that animal from flea infestation. As will be disclosed in more detail below, a nucleic acid molecule of the present invention can be, or encode, an antisense RNA, a molecule capable of triple helix formation, a ribozyme, or other nucleic acid-based drug compound. In additional embodiments, a nucleic acid molecule of the present invention can encode a protective protein (e.g., a flea allantoinase protein of the present invention), the nucleic acid molecule being delivered to the animal, for example, by direct injection (i.e, as a genetic vaccine) or in a vehicle such as a recombinant virus vaccine or a recombinant cell vaccine.

In one embodiment of the present invention, a preferred flea allantoinase nucleic acid molecule includes an isolated nucleic acid molecule that hybridizes under conditions that preferably allow less than or equal to 30% base pair mismatch, preferably under conditions that allow less than or equal to 20% base pair mismatch, preferably under conditions that allow less than or equal to 10% base pair mismatch preferably under conditions that allow less than or equal to 5% base pair mismatch or preferably under conditions that allow less than or equal to 2% base pair mismatch with a nucleic acid molecule selected from the group consisting of SEQ ID NO:1, SEQ ID NO:3, SEQ ID NO:4, SEQ ID NO:5, SEQ ID NO:6, SEQ ID NO:8, SEQ ID NO:9, and SEQ ID NO:11.

Another embodiment of the present invention includes a flea allantoinase nucleic acid molecule, wherein said nucleic acid molecule hybridizes under conditions comprising, (a) hybridizing in solution comprising 1×SSC in the absence of nucleic acid helix destabilizing compounds, at a temperature of 37° C. and (b) washing in a solution comprising 1×SSC in the absence of nucleic acid helix destabilizing compounds, at a temperature of 47° C., to an isolated nucleic acid molecule selected from the group consisting of SEQ ID NO:1, SEQ ID NO:3, SEQ ID NO:4, SEQ ID NO:5, SEQ ID NO:6, SEQ ID NO:8, SEQ ID NO:9, and SEQ ID NO:11. Additional preferred nucleic acid molecules of the present invention include oligonucleotides of an isolated nucleic acid molecule, wherein said nucleic acid molecule hybridizes under conditions comprising, (a) hybridizing in solution comprising IX SSC in the absence of nucleic acid helix destabilizing compounds, at a temperature of 37° C. and (b) washing in a solution comprising 1×SSC in the absence of nucleic acid helix destabilizing compounds, at a temperature of 47° C., to an isolated nucleic acid molecule selected from the group consisting of SEQ ID NO:1, SEQ ID NO:3, SEQ ID NO:4, SEQ ID NO:5, SEQ ID NO:6, SEQ ID NO:8, SEQ ID NO:9, and SEQ ID NO:11, wherein said oligonucleotide comprises at least 30 nucleotides.

Additional preferred flea allantoinase nucleic acid molecules of the present invention include nucleic acid molecules comprising a nucleic acid sequence that is preferably at least 70%, preferably at least 80%, preferably at least 90%, preferably at least 92%, preferably at least 95%, or preferably at least 98% identical to a nucleic acid sequence selected from the group consisting of SEQ ID NO:1, SEQ ID NO:3, SEQ ID NO:4, SEQ ID NO:5, SEQ ID NO:6, SEQ ID NO:8, SEQ ID NO:9, and SEQ ID NO:11. Also preferred are oligonucleotides of any of such nucleic acid molecules. Percent identity as used herein is determined using the Needleman-Wunsch algorithm, available in the SeqLab software using default parameters.

One embodiment of the present invention is a nucleic acid molecule comprising -all or part of nucleic acid molecules $nCfALN_{2035}$, nCfALN1449, $nCfALN_{1383}$, and $nCfALN_{1123}$, or allelic variants of these nucleic acid molecules. Another preferred nucleic acid molecule of the present invention includes at least a portion of nucleic acid sequence SEQ ID NO:1, SEQ ID NO:3, SEQ ID NO:4, SEQ ID NO:5, SEQ ID NO:6, SEQ ID NO:8, SEQ ID NO:9, and SEQ ID NO:11, as well as allelic variants of nucleic acid molecules having these nucleic acid sequences and homologues of nucleic acid molecules having these nucleic acid sequences; preferably such a homologue encodes or is complementary to a nucleic acid molecule that encodes at least one epitope that elicits an immune response against a protein having an amino acid sequence SEQ ID NO:2, SEQ ID NO:7 and SEQ ID NO:10. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

In one embodiment, a flea allantoinase nucleic acid molecule of the present invention encodes a protein having an amino acid sequence that is at least 70%, preferably at least 80%, preferably at least 90%, preferably at least 95%, preferably at least 98%, preferably at least 99%, or preferably at least 100% identical to SEQ ID NO:2, SEQ ID NO:7 and SEQ ID NO:10. The present invention also includes a flea allantoinase nucleic acid molecule encoding a protein having at least a portion of SEQ ID NO:2, SEQ ID NO:7 and SEQ ID NO:10, as well as allelic variants of a nucleic acid molecule encoding a protein having these sequences, including nucleic acid molecules that have been modified to accommodate codon usage properties of the cells in which such nucleic acid molecules are to be expressed.

In another embodiment, a preferred flea allantoinase nucleic acid molecule of the present invention comprises a nucleic acid molecule comprising at least 20 nucleotides, preferably at least 25 nucleotides, preferably at least 30 nucleotides, preferably at least 40 nucleotides, preferably at least 50 nucleotides, preferably at least 75 nucleotides, preferably at least 100 nucleotides, preferably at least 200 nucleotides, preferably at least 400 nucleotides, preferably at least 500 nucleotides, preferably at least 750 nucleotides, preferably at least 1000 nucleotides, preferably at least 1500 nucleotides, preferably at least 1800 nucleotides, preferably at least 2000 nucleotides, or preferably at least 2035 nucleotides in length.

In another embodiment, a preferred flea allantoinase nucleic acid molecule encodes a protein comprising at least 6 amino acids, preferably at least 10 amino acids, preferably at least 20 amino acids, preferably at least 30 amino acids, preferably at least 40 amino acids, preferably at least 50 amino acids, preferably at least 75 amino acids, preferably at least 100 amino acids, preferably at least 125 amino acids, preferably at least 150 amino acids, preferably at least 175 amino acids, preferably at least 200 amino acids, preferably at least 250 amino acids, preferably at least 300 amino acids, preferably at least 350 amino acids, preferably at least 400 amino acids, preferably at least 450 amino acids, preferably at least 460 amino acids, or preferably at least 483 amino acids.

In another embodiment, a preferred flea allantoinase nucleic acid molecule of the present invention comprises an apparently full-length flea allantoinase coding region, i.e., the preferred nucleic acid molecule encodes an apparently full-length flea allantoinase protein, respectively, or a post-translationally modified protein thereof. In one embodiment, a preferred flea allantoinase nucleic acid molecule of the present invention encodes a mature protein.

In another embodiment, a preferred flea allantoinase nucleic acid molecule of the present invention comprises a nucleic acid molecule comprising SEQ ID NO:1, SEQ ID NO:3, SEQ ID NO:4, SEQ ID NO:5, SEQ ID NO:6, SEQ ID NO:8, SEQ ID NO:9, and SEQ ID NO:11, or a fragment thereof.

A fragment of a flea allantoinase nucleic acid molecule of the present invention preferably comprises at least 18 nucleotides, preferably at least 21 nucleotides, preferably at least 25 nucleotides, preferably at least 30 nucleotides, preferably at least 35 nucleotides, preferably at least 40 nucleotides, preferably at least 50 nucleotides, preferably at least 75 nucleotides, preferably at least 100 nucleotides, preferably at least 200 nucleotides, preferably at least 400 nucleotides, preferably at least 500 nucleotides, preferably at least 750 nucleotides, preferably at least 1000 nucleotides, preferably at least 1500 nucleotides, preferably at least 1800 nucleotides, preferably at least 2000 nucleotides, or preferably at least 2035 nucleotides identical in sequence to a corresponding contiguous sequence selected from the group consisting of SEQ ID NO:1, SEQ ID NO:3, SEQ ID NO:4, SEQ ID NO:5, SEQ ID NO:6, SEQ ID NO:8, SEQ ID NO:9, and SEQ ID NO:11.

The phrase, a nucleic acid molecule comprising at least "x" contiguous, or consecutive nucleotides identical in sequence to at least "x" contiguous, or consecutive nucleotides of a nucleic acid molecule selected from the group consisting of SEQ ID NO:"y", refers to an "x"-nucleotide in length nucleic acid molecule that is identical in sequence to an "x"-nucleotide portion of SEQ ID NO:"y", as well as to nucleic acid molecules that are longer in length than "x". The additional length may be in the form of nucleotides that extend from either the 5' or the 3' end(s) of the contiguous identical "x"-nucleotide portion. The 5' and/or 3' extensions can include one or more extensions that have no identity to a molecule of the present invention, as well as extensions that show similarity or identity to cited nucleic acids sequences or portions thereof.

Knowing the nucleic acid sequences of certain flea allantoinase nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other flea allantoinase nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include cDNA libraries as well as genomic DNA libraries. Similarly, preferred DNA sources to screen or from which to amplify nucleic acid molecules include cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising *C. felis* allantoinase nucleic acid molecules or other flea allantoinase nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of preferably 100 to 200 nucleotides. The present invention includes oligonucleotides that can be used as, for example, probes to identify nucleic acid molecules, primers to produce nucleic acid molecules, or therapeutic reagents to inhibit flea allantoinase protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of flea allantoinase nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, insect and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences that control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those that function in bacterial, yeast, or insect and mammalian cells, such as, but not limited to, tac, lac, trp, trc, oxy-pro, omp/lpp, rrnB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, *Pichia* alcohol oxidase, alphavirus subgenomic promoter, antibiotic resistance gene, baculovirus, *Heliothis zea* insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with fleas, such as *C. felis* transcription control sequences.

Suitable and preferred nucleic acid molecules to include in recombinant vectors of the present invention are as disclosed herein. Preferred nucleic acid molecules to include in recombinant vectors, and particularly in recombinant molecules, include $nCfALN_{2035}$, $nCfALN_{1449}$, $nCfAL_{1383}$, and $nCfALN_{1123}$.

Recombinant molecules of the present invention may also (a) contain secretory signals (i.e., signal segment nucleic acid sequences) to enable an expressed flea allantoinase protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. It is to be noted that a cell line refers to any recombinant cell of the present invention that is not a transgenic animal. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include flea allantoinase nucleic acid molecules disclosed herein. Preferred nucleic acid molecules with which to transform a cell include $nCfALN_{2035}$, $nCfALN_{1449}$, $nCfALN_{1383}$, and $nCfALN_{1123}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing flea allantoinase proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, insect and mammalian cells. More preferred host cells include *Salmonella, Escherichia, Bacillus, Caulobacter, Listeria, Saccharomyces, Pichia, Spodoptera, Mycobacteria, Trichoplusia*, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1$_x$3987 and SR-11$_x$4072; *Caulobacter; Pichia; Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein. The phrase operatively linked refers to insertion of a nucleic acid molecule into an expression vector in a manner such that the molecule is able to be expressed when transformed into a host cell.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including flea allantoinase nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated flea allantoinase proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a flea allantoinase protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a flea allantoinase protein of the present invention or a mimetope thereof (e.g., anti-flea allantoinase antibodies). As used herein, the term "selectively binds to" a protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual*, Cold Spring Harbor Labs Press; Harlow et al., ibid., is incorporated by reference herein in its entirety. An anti-flea allantoinase antibody of the present invention preferably selectively binds to a flea allantoinase protein, respectively, in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce flea allantoinase proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from fleas susceptible to treatment by such antibodies and/or (b) as tools to screen expression libraries and/or to recover desired proteins of the present invention from a mixture of proteins and other contaminants. Furthermore, antibodies of the present invention can be used to target cytotoxic agents to fleas in order to directly kill such fleas. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal susceptible to flea infestation, is capable of protecting that animal from flea infestation. Therapeutic compositions of the present invention include at least one of the following protective molecules: an isolated flea allantoinase protein; a mimetope of an isolated flea allantoinase protein; an isolated flea allantoinase nucleic acid molecule; and/or a compound derived from said isolated flea allantoinase protein that inhibits flea allantoinase protein activity. A therapeutic composition of the present invention can further comprise a component selected from the group of an excipient, a carrier, and/or an adjuvant; these components are described further herein. As used herein, a protective molecule or protective compound refers to a compound that, when administered to an animal in an effective manner, is able to treat, ameliorate, and/or prevent flea infestation. Preferred fleas to target are heretofore disclosed. One example of a protective molecule is a vaccine, such as, but not limited to, a naked nucleic acid vaccine, a recombinant virus vaccine, a recombinant cell vaccine, and a recombinant protein vaccine. Another example of a protective molecule is a compound that inhibits flea allantoinase protein activity, such as an isolated antibody that selectively binds to a flea allantoinase protein, a substrate analog of a flea allantoinase protein, anti-sense-, triplex formation-, ribozyme-, and/or RNA drug-based compounds, or other inorganic or organic molecules that inhibit flea allantoinase protein activity. Inhibiting flea allantoinase protein activity can refer to the ability of a compound to reduce the activity of flea allantoinase proteins. Inhibiting flea allantoinase protein activity can also refer to the ability of a compound to reduce the amount of flea allantoinase protein in a flea One embodiment of the present invention is a therapeutic composition comprising an excipient and a compound selected from the group consisting of: (a) an isolated nucleic acid molecule selected from the group consisting of a flea cDNA molecule and a flea mRNA molecule, wherein said nucleic acid molecule is at least 30 nucleotides in length and hybridizes with a nucleic acid molecule having a nucleic acid sequence selected from the group consisting of SEQ ID NO:1, SEQ ID NO:3, SEQ ID NO:4, SEQ ID NO:5, SEQ ID NO:6, SEQ ID NO:8, SEQ ID NO:9, and SEQ ID NO:11, under conditions comprising (1) hybridizing in a solution comprising 1×SSC in the absence of nucleic acid helix destabilizing compounds, at a temperature of 37° C. and (2) washing in a solution comprising 1×SSC in the absence of helix destabilizing compounds, at a temperature of 47° C.; (b) an isolated protein encoded by a nucleic acid molecule at least 30 nucleotides in length that hybridizes with a nucleic acid molecule having a nucleic acid sequence selected from the group consisting of SEQ ID NO:3, SEQ ID NO:5, SEQ ID NO:8 and SEQ ID NO:11, under conditions comprising (i) hybridizing in a solution comprising 1×SSC in the absence of helix destabilizing compounds, at a temperature of 37° C. and (ii) washing in a solution comprising 1×SSC in the absence of helix destabilizing compounds, at a temperature of 47° C.; and (c) an isolated antibody that selectively binds to a protein of (b).

Another embodiment of the present invention includes a method to reduce flea infestation in an animal susceptible to flea infestation. Such a method includes the step of administering to the animal a therapeutic molecule comprising a protective compound selected from the group consisting of (a) an isolated flea allantoinase protein; (b) a mimetope of an isolated flea allantoinase protein; (c) an isolated flea allantoinase nucleic acid molecule; and (d) a compound derived from an isolated flea allantoinase protein that inhibits flea allantoinase protein activity.

Therapeutic compositions of the present invention can be administered to any animal susceptible to flea infestation, preferably to mammals, and more preferably to dogs, cats, humans, ferrets, horses, cattle, sheep, and other pets, economic food animals, work animals and/or zoo animals. Preferred animals to protect against flea infestation include dogs, cats, humans, and ferrets, with dogs and cats being particularly preferred.

As used herein, the term derived, or the term derived from, refers to a peptide, antibody, mimetope, nucleic acid molecule, or other compound that was obtained from or obtained using a flea allantoinase protein or nucleic acid molecule of the present invention. Methods to obtain derivatives from a flea allantoinase molecule of the present invention are known in the art, and as such include, but are not limited to molecular modeling of flea allantoinase proteins to determine active sites, and predicting from these active sites smaller fragments and/or mimetopes that retain and/or mimic these active sites, thereby inhibiting flea allantoinase protein activity. Other inhibitors of flea allantoinase activity can also be obtained in a variety of ways, including but not limited to screening of peptide or small chemical compound libraries against flea allantoinase proteins of the present invention; and screening of polyclonal or monoclonal antibodies to find antibodies that specifically bind flea allantoinase proteins of the present invention.

A flea allantoinase protein inhibitor of the present invention (i.e. an inhibitor of a flea allantoinase protein) is identified by its ability to mimic, bind to, modify, or otherwise interact with, a flea allantoinase protein, thereby inhibiting the activity of a natural flea allantoinase protein. Suitable inhibitors of flea allantoinase protein activity are compounds that inhibit flea allantoinase protein activity in at least one of a variety of ways: (a) by binding to or otherwise interacting with or otherwise modifying flea allantoinase protein sites; (b) by binding to the flea allantoinase protein and thus reducing the availability of the flea allantoinase protein in solution; (c) by mimicking a flea allantoinase protein; and (d) by interacting with other regions of the flea allantoinase protein to inhibit flea allantoinase protein activity, for example, by allosteric interaction.

Flea allantoinase protein inhibitors can be used directly as compounds in compositions of the present invention to treat animals as long as such compounds are not harmful to host animals being treated. Preferred flea allantoinase protein inhibitors of the present invention include, but are not limited to, flea allantoinase protein substrate analogs, and other molecules that bind to a flea allantoinase protein (e.g., to an allosteric site) in such a manner that the activity of the flea allantoinase protein is inhibited. A flea allantoinase protein substrate analog refers to a compound that interacts with (e.g., binds to, associates with, modifies) the active site of a flea allantoinase protein. A preferred flea allantoinase protein substrate analog inhibits flea allantoinase protein activity. Flea allantoinase protein substrate analogs can be of any inorganic or organic composition. Flea allantoinase protein substrate analogs can be, but need not be, structurally similar to a flea allantoinase protein natural substrate as long as they can interact with the active site of that flea allantoinase protein. Flea allantoinase protein substrate analogs can be designed using computer-generated structures of flea allantoinase proteins of the present invention or computer structures of flea allantoinase protein's natural substrates. Preferred sites to model include one or more of the active sites of flea allantoinase proteins. Substrate analogs can also be obtained by generating random samples of molecules, such as oligonucleotides, peptides, peptidomimetic compounds, or other inorganic or organic molecules, and screening such samples for their ability to interfere with interaction between flea allantoinase proteins and their substrates, e.g. by affinity chromatography techniques. A preferred flea allantoinase protein substrate analog is a flea allantoinase protein mimetic compound, i.e., a compound that is structurally and/or functionally similar to a natural substrate of a flea allantoinase protein of the present invention, particularly to the region of the substrate that interacts with the flea allantoinase protein active site, but that inhibits flea allantoinase protein activity upon interacting with the flea allantoinase protein active site.

The present invention also includes a therapeutic composition comprising at least one protective molecule of the present invention in combination with at least one additional compound protective against one or more infectious agents.

In one embodiment, a therapeutic composition of the present invention can be used to protect an animal from flea infestation by administering such composition to a flea in order to prevent infestation. Such administration to the flea and/or animal could be oral, or by application to the animal's body surface (e.g. topical spot-on, or spraying onto the animal), or by application to the environment (e.g., spraying). Examples of such compositions include, but are not limited to, transgenic vectors capable of producing at least one therapeutic composition of the present invention. In another embodiment a flea can ingest therapeutic compositions, or products thereof, present on the surface of or in the blood of a host animal that has been administered a therapeutic composition of the present invention.

In accordance with the present invention, a host animal (i.e., an animal that is or is capable of being infested with fleas) is treated by administering to the animal a therapeutic composition of the present invention in such a manner that the composition itself (e.g., a flea allantoinase protein, a flea allantoinase nucleic acid molecule, a flea allantoinase protein inhibitor, a allantoinase protein synthesis suppressor (i.e., a compound that decreases the production or half-life of a allantoinase protein in fleas), a flea allantoinase protein mimetope, or a anti-flea allantoinase antibody) or a product generated by the animal in response to administration of the composition (e.g., antibodies produced in response to administration of a flea allantoinase protein or nucleic acid molecule, or conversion of an inactive inhibitor "prodrug" to an active flea allantoinase protein inhibitor) ultimately enters the flea. A host animal is preferably treated in such a way that the compound or product thereof is present on the body surface of the animal or enters the blood stream of the animal. Fleas are then exposed to the composition or product when they feed from the animal. For example, flea allantoinase protein inhibitors administered to an animal are administered in such a way that the inhibitors enter the blood stream of the animal, where they can be taken up by feeding fleas.

The present invention also includes the ability to reduce larval flea infestation in that when fleas feed from a host animal that has been administered a therapeutic composition of the present invention, at least a portion of compounds of the present invention, or products thereof, in the blood taken up by the fleas are excreted by the fleas in feces, which is subsequently ingested by flea larvae. In particular, it is of note that flea larvae obtain most, if not all, of their nutrition from flea feces.

In accordance with the present invention, reducing flea allantoinase protein activity in a flea can lead to a number of outcomes that reduce flea burden on treated animals and their surrounding environments. Such outcomes include, but are not limited to, (a) reducing the viability of fleas that feed from the treated animal, (b) reducing the fecundity of female fleas that feed from the treated animal, (c) reducing the reproductive capacity of male fleas that feed from the treated animal, (d) reducing the viability of eggs laid by female fleas that feed from the treated animal, (e) altering the blood feeding behavior of fleas that feed from the treated animal (e.g., fleas take up less volume per feeding or feed less frequently), (f) reducing the viability of flea larvae, for example due to the feeding of larvae from feces of fleas that feed from the treated animal, (g) altering the development of flea larvae (e.g., by decreasing feeding behavior, inhibiting growth, inhibiting (e.g., slowing or blocking) molting, and/ or otherwise inhibiting maturation to adults), and/or (h) altering or decreasing the ability of fleas or flea larvae to digest a blood meal.

In order to protect an animal from flea infestation, a therapeutic composition of the present invention is administered to the animal in an effective manner such that the composition is capable of protecting that animal from flea infestation. Therapeutic compositions of the present invention can be administered to animals prior to infestation in order to prevent infestation (i.e., as a preventative vaccine) and/or can be administered to animals after infestation. For example, proteins, mimetopes thereof, and antibodies thereof can be used as immunotherapeutic agents.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), Flt-3 ligand, granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL4), interleukin 5 (IL5), interleukin 6 (IL-6), interleukin 7 (IL-7), interleukin 8 (IL-8), interleukin 10 (IL10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition. The therapeutic composition is preferably released over a period of time ranging from 1 to 12 months. A controlled release formulation of the present invention is capable of effecting a treatment preferably for at least 1 month, preferably for at least 3 months, preferably for at least 6 months, preferably for at least 9 months, and preferably for at least 12 months.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of treating an animal when administered one or more times over a suitable time period. For example, a preferred single dose of an inhibitor is from about 1 microgram ($\mu$g) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal, intraocular, intranasal, conjunctival, and intramuscular routes. Methods of administration for other therapeutic compounds can be determined by one skilled in the art, and may include administration of a therapeutic composition one or more times, on a daily, weekly, monthly or yearly regimen; routes of administration can be determined by one skilled in the art, and may include any route. A preferred route of administration of an inhibitory compound when administering to fleas is a topical, or "spot-on" formulation administered to the body surface of the animal, so that a flea would encounter the inhibitory compound when attached to the animal; another preferred route of administration of an inhibitory compound is an oral formulation that, when fed to an animal, would enter the bloodstream of the animal, which would then be transferred to a flea while feeding from the animal.

A recombinant protein vaccine of the present invention comprises a recombinantly-produced flea allantoinase protein of the present invention that is administered to an animal according to a protocol that results in the animal producing a sufficient immune response to protect itself from a flea infestation. Such protocols can be determined by those skilled in the art.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid as a genetic vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. Preferred genetic vaccines include at least a portion of a viral genome, i.e., a viral vector. Preferred viral vectors include those based on alphaviruses, poxviruses, adenoviruses, herpesviruses, picornaviruses, and retroviruses, with those based on alphaviruses, such as sindbis or Semliki forest virus, species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal, conjunctival, intraocular, intranasal and oral routes of administration being preferred. A preferred single dose of a genetic vaccine ranges from about 1 nanogram (ng) to about 600 µg, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses (such as Sindbis virus), raccoon poxviruses, species-specific herpesviruses and species-specific poxviruses. An example of methods to produce and use alphavirus recombinant virus vaccines are disclosed in U.S. Pat. No. 5,766,602 to Xiong and Grieve, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from flea infestation as disclosed herein. For example, a recombinant virus vaccine comprising a flea allantoinase nucleic acid molecule of the present invention is administered according to a protocol that results in the animal producing a sufficient immune response to protect itself from flea infestation. A preferred single dose of a recombinant virus vaccine of the present invention is from about $1 \times 10^4$ to about $1 \times 10^3$ virus plaque forming units (pfu) per kilogram body weight of the animal. Administration protocols are similar to those described herein for protein-based vaccines, with subcutaneous, intramuscular, intranasal, intraocular, conjunctival, and oral administration routes being preferred.

A recombinant cell vaccine of the present invention includes recombinant cells of the present invention that express at least one protein of the present invention. Preferred recombinant cells for this embodiment include *Salmonella, E. coli, Listeria, Mycobacterium, S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from flea infestation can be tested in a variety of ways including, but not limited to, detection of protective antibodies (using, for example, proteins or mimetopes of the present invention), detection of cellular immunity within the treated animal, or challenge of the treated animal with the fleas to determine whether the treated animal is resistant to infestation. Challenge studies can include direct administration of fleas to the treated animal. In one embodiment, therapeutic compositions can be tested in animal models such as mice. Such techniques are known to those skilled in the art.

As discussed herein, one therapeutic composition of the present invention includes an inhibitor of flea allantoinase protein activity, i.e., a compound capable of substantially interfering with the function of a flea allantoinase protein. An inhibitor of flea allantoinase protein activity, or function, can be identified using flea allantoinase proteins of the present invention. A preferred inhibitor of flea allantoinase protein function is a compound capable of substantially interfering with the function of a flea allantoinase protein and which does not substantially interfere with the function of host animal allantoinase proteins. As used herein, a compound that does not substantially inhibit or interfere with host animal allantoinase proteins is one that, when administered to a host animal, the host animal shows no significant adverse effects attributable to the inhibition of allantoinase and which, when administered to an animal in an effective manner, is capable of protecting that animal from flea infestation.

One embodiment of the present invention is a method to identify a compound capable of inhibiting flea allantoinase protein activity. Such a method includes the steps of (a) contacting (e.g., combining, mixing) an isolated flea allantoinase protein of the present invention, such as a flea extract having allantoinase activity, with a putative inhibitory compound under conditions in which, in the absence of the compound, the protein has flea allantoinase protein activity, and (b) determining if the putative inhibitory compound inhibits the activity. Flea allantoinase protein activity can be determined in a variety of ways known in the art, including but not limited to determining the ability of flea allantoinase protein to bind to or otherwise interact with a substrate. Such conditions under which a flea allantoinase protein has flea allantoinase protein activity include conditions in which a flea allantoinase protein has a correct three-dimensionally folded structure under physiologic conditions, i.e. physiologic pH, physiologic ionic concentrations, and physiologic temperatures.

Putative inhibitory compounds to screen include antibodies (including fragments and mimetopes thereof), putative substrate analogs, and other, preferably small, organic or inorganic molecules. Methods to determine flea allantoinase protein activity are known to those skilled in the art.

A preferred method to identify a compound capable of inhibiting flea allantoinase protein activity includes contacting an isolated flea allantoinase protein of the present invention with a putative inhibitory compound under conditions in which, in the absence of the compound, the protein has flea allantoinase protein activity; and determining if the putative inhibitory compound inhibits the activity.

Another embodiment of the present invention is an assay kit to identify an inhibitor of a flea allantoinase protein of the present invention. This kit comprises an isolated flea allantoinase protein of the present invention, and a means for determining inhibition of an activity of flea allantoinase protein, where the means enables detection of inhibition. Detection of inhibition of flea allantoinase protein identifies a putative inhibitor to be an inhibitor of a flea allantoinase protein. Means for determining inhibition of a flea allantoinase protein include, for example, an assay system that detects binding of a putative inhibitor to a flea allantoinase molecule, and an assay system that detects interference by a putative inhibitor of the ability of flea allantoinase protein to hydrolyze a substrate. Means and methods are described herein and are known to those skilled in the art.

The following examples are provided for the purposes of illustration and are not intended to limit the scope of the present invention. The following examples include a number of recombinant DNA and protein chemistry techniques known to those skilled in the art; see, for example, Sambrook et al., ibid.

EXAMPLE 1

This Example describes the isolation of RNA from the hindgut and Malpighian tubules (HMT) of *Ctenocephalides felis* and the use of isolated RNA to construct subtracted and unsubtracted cDNA libraries.

Approximately 10,000 hindguts and Malpighian tubules were dissected from equal numbers of cat blood fed and unfed adult *C. felis* with a male to female ratio of 1 to 4, and total RNA was extracted using a guanidine isothiocyanate lysis buffer and the standard procedure described by Sambrook et al. Poly-A enriched mRNA was purified from total RNA above using a mRNA Purification Kit, available from Pharmacia Biotech, Piscataway, N.J., following the manufacturer's protocol. The same procedures were used to extract total RNA and isolate poly-A enriched mRNA from the dissected *C. felis* bodies following removal of HMT, referred to hereinafter as "non-HMT mRNA".

Poly-A enriched mRNA was used to construct a cDNA library using subtractive hybridization and suppression PCR as follows. Subtractive hybridization and suppression PCR was conducted using a PCR-Select™ cDNA Subtraction Kit, available from Clontech Laboratories, Inc., Palo Alto, Calif. according to the manufacturer's instructions. Briefly, this kit uses subtractive hybridization and suppression PCR to specifically amplify cDNA sequences that are present in the tester cDNA and absent in the driver cDNA, thus enriching for tester-specific sequences. The efficiency of the subtraction process can be assessed by semi-quantitative PCR and by comparing the ethidium bromide staining patterns of the subtracted and unsubtracted samples on agarose gels as described in section V.D. of the manufacturer's protocol. For the semi-quantitative PCR, three genes with mRNAs known to be expressed outside of the HMT tissue were used to test for specific subtraction. These genes encoded putative actin, N-aminopeptidase, and serine protease proteins.

Subtractive hybridization and suppression PCR was conducted under the following conditions. Two micrograms (μg) of HMT mRNA was used as the template for synthesis of the tester material and 2 μg of non-HMT mRNA was used as template for synthesis of the driver material in this reaction. The number of cycles used in the selective amplification steps was optimized using the manufacturer's protocols. Optimization resulted in the use of 24 rather than the standard 27 cycles of primary PCR in combination with 15 cycles of secondary PCR rather than the standard 12 cycles.

The products from the suppressive PCR reaction were ligated into the pCR®2.1 vector, available from Invitrogen, Carlsbad, Calif., using an Original TA Cloning® Kit, available from Invitrogen. The ligation reaction was then used to transform INVαF[1] One Shot™ competent cells, available from Invitrogen, which were plated on Luria broth (LB) agar with 50 micrograms per milliliter (μg/ml) ampicillin, available from Sigma-Aldrich Co., St. Louis, Mo., and 50 μg/ml 5-bromo-4-chloro-3-indoyl β-D-galactopyranoside (X-Gal), available from Fisher Biotech, Fair Lawn, N.J. Transformed colonies were amplified and the DNA isolated using the standard alkaline lysis procedure described by Sambrook et al., ibid.

Automated cycle sequencing of DNA samples was performed using an ABI PRISM™ Model 377, available from Perkins Elmer, with XL upgrade DNA Sequencer, available from PE Applied Biosystems, Foster City, Calif., after reactions were carried out using the PRISM™ Dye Terminator Cycle Sequencing Ready Reaction Kit or the PRISM™ dRhodamine Terminator Cycle Sequencing Ready Reaction Kit or the PRISM™ BigDye™ Terminator Cycle sequencing Ready Reaction Kit, available from PE Applied Biosystems, following the manufacturer's protocol, hereinafter "standard sequencing methods". Sequence analysis was performed using SeqLab, using default parameters. Each sequence read was trimmed of vector sequence at either end and submitted for a search through the National Center for Biotechnology Information (NCBI), National Library of Medicine, National Institute of Health, Baltimore, Md., using the BLAST network. This database includes SwissProt+PIR+ SPupdate+GenPept+GPUpdate+PDB databases. The search was conducted using the xBLAST function, which compares the translated sequences in all 6 reading frames to the protein sequences contained in the database.

An unsubtracted HMT cDNA library was constructed as follows. Approximately 10,000 HMT tissues were dissected from equal numbers of unfed and cat blood-fed adult *C. felis* with a male to female ratio of 1:4. Total RNA was extracted using a guanidine isothiocyanate lysis buffer and procedures described in Sambrook et al., followed by isolation using a mRNA purification kit, available from Pharmacia, according to the manufacturer's protocols. The library was constructed with 5 μg of isolated mRNA using a ZAP-cDNA® cDNA synthesis kit, and packaged using a ZAP-cDNA® Gigapack® gold cloning kit, both available from Stratagene, La Jolla, Calif. The resultant HMT library was amplified to a titer of about $5 \times 10^9$ plaque forming units per milliliter (pfu/ml). Single clone excisions were performed using the Ex-Assist™ helper phage, available from Stratagene, and used to create double stranded plasmid template for sequencing using the manufacturer's protocols with the following exceptions. Following incubation of the SOLR cells with the cleared phage lysate, the mixture was used to inoculate LB broth, and the mix was incubated overnight and then subjected to mini-prep plasmid preparation and sequencing as described for the subtracted HMT library above.

EXAMPLE 2

This example describes the cloning and sequencing of a *C. felis* allantoinase nucleic acid molecule of the present invention and expression and purification of recombinant protein therefrom. This example also describes the expression of allantoinase mRNA in a variety of flea tissues, activity assays of native proteins, the production of affinity purified antibody to a recombinant flea allantoinase protein, and protein localization by immunohistochemistry.

A. Isolation of Nucleic Acid Sequences

A TA clone from the HMT EST library described in Example 1 was sequenced using standard sequencing methods and shown to encode a partial polypeptide having significant homology to allantoinase proteins. This clone was digested with EcoRI to excise an insert 682 nucleotides in length, referred to as flea nucleic acid molecule nCfALN$_{682}$. The insert was isolated by gel purification using a Gel Purification kit, available from Qiagen, Chatsworth, Calif. Approximately 50 nanograms (ng) of purified nCfALN$_{682}$ was used to construct a $^{32}$P α-dATP labeled DNA probe using a Megaprime DNA labeling kit, available from Amersham, Arlington Heights, Ill., using the manufacturer's protocols.

The $^{32}$P α-dATP labeled probe was used in a plaque lift hybridization procedure to isolate a clone from the HMT lambda-ZAP unsubtracted cDNA library described in Example 1 under the following hybridization conditions. Filters were hybridized with about $1 \times 10^6$ counts per minute (cpm) per ml of the probe in 5×SSPE, (see Sambrook et al., ibid.), 1.2% sodium dodecyl sulfate (SDS), 0.1 mg/ml salmon sperm DNA and 5× Denhardt's reagent, (see Sambrook et al., ibid.), at 55° C. for about 14 hours. The filters were washed as follows: (a) 10 minutes with 5×SSPE and 1% SDS, (b) 10 minutes with 2×SSPE and 1% SDS, (c) 10 minutes with 1×SSPE and 0.5% SDS, and (d) 10 minutes with 0.5×SSPE and 1% SDS. All washes were conducted at 55° C. Plaques that hybridized strongly to the probe were isolated and subjected to in vivo excision. In vivo excision was performed using the Stratagene Ex-Assist™ helper phage system and protocols, to convert a positive plaque to pBluescript™ plasmid DNA. Sequencing was conducted using standard sequencing methods following preparation of DNA with a Qiagen Qiaprep™ spin mini prep kit using the manufacturer's instructions and restriction enzyme digestion with about 1 μl of 20 U/μl each of EcoRI and XhoI, available from New England Biolabs, Beverly, Mass. A clone was isolated from a primary plaque, containing a nucleic acid molecule of about 2035 base pairs, referred to herein as nCfALN$_{2035}$, the coding strand of which is a nucleotide sequence denoted herein as SEQ ID NO:1. The complement of SEQ ID NO:1 is represented herein as SEQ ID NO:3.

The clone containing SEQ ID NO:1 was originally sequenced and named nCfALN$_{2057}$, see PCT Publication WO 00/61621. Upon re-sequencing of nCfALN$_{2057}$ it was determined that a sequencing error occurred, resulting in the insertion of a guanine at position 1292. SEQ ID NO:1 also reflects the removal of a poly-A tail in the 3' untranslated region of the molecule, but otherwise nCfALN$_{2057}$ and nCfALN$_{2035}$ are identical.

Translation of SEQ ID NO:1 suggests that nucleic acid molecule nCfALN$_{2035}$ encodes a full-length allantoinase protein of 483 amino acids, referred to herein as PCfALN$_{483}$, the amino acid sequence of which is represented by SEQ ID NO:2, assuming the initiation codon spans from nucleotide 152 through nucleotide 154 of SEQ ID NO:1 and the termination codon spans from nucleotide 1601 through nucleotide 1603 of SEQ ID NO:1. The coding region encoding PCfALN$_{483}$, is represented by nucleic acid molecule nCfALN$_{1449}$, having a coding strand with the nucleic acid sequence represented by SEQ ID NO:4 and a complementary strand with nucleic acid sequence represented by SEQ ID NO:5. The amino acid sequence of PCfALN$_{483}$, also represented as SEQ ID NO:2, predicts that PCfALN$_{483}$ has an estimated molecular weight of about 53 kilodaltons (kDa) and an estimated isoelectric point (pI) of about 6.34.

Comparison of amino acid sequence SEQ ID NO:2 with amino acid sequences reported in GenBank indicates that SEQ ID NO:2 showed the most homology, i.e., about 45.7% identity, with a Streptomyces coelicolor "probable allantoinase" protein GenBank Accession No. Q9RKU5, and a second highest homology, i.e. about 45.1% identity to a *Rana catesbeiana* (bullfrog) allantoinase protein, GenBank Accession No. 458126. Comparison of SEQ ID NO:4 with nucleic acid sequences reported in GenBank indicates that SEQ ID NO:4 showed the most homology, i.e., about 51% identity, with a *Rana catesbeiana* nucleic acid molecule, GenBank Accession number U03471. Percent identity calculations were performed using GCG version 9.0 using default parameters.

B. Protein Expression

The region of nCfALN$_{2035}$ encoding the predicted mature protein, referred to herein as nCfALN$_{1383}$, the coding strand of which is a nucleotide sequence designated SEQ ID NO:6 and a complementary strand designated SEQ ID NO:8, was PCR amplified using the pBluescript™ clone described above as the template. Sense primer ALLA-FE, having nucleotide sequence 5' CAT GCC ATG GCG TGC ACC AAC AAC GCG CCT CC 3', having a NcoI site indicated in bold, designated herein as SEQ ID NO:12, and anti-sense primer ALLA-RE, having nucleotide sequence 5' GCG GTA CCT CAT TCA ATA AGT AAA TTT CCT TTT GG 3', having a KpnI site indicated in bold, designated herein as SEQ ID NO:13 were used in the PCR reaction. PCR reactions were performed using the following amplification cycles: (a) one cycle at 95° C. for thirty seconds; (b) thirty cycles at 95° C. for twenty seconds, 50° C. for twenty seconds, and 72° C. for two minutes; and (c) one cycle at 72° C. for five minutes, in reactions containing 2.5 mM $MgCl_2$, 0.2 mM dNTPs, 1 µM of each primer, 0.5 µl of 5 U/µl Taq polymerase, 1 µl of 1 µg/µl template, and 3 µl of 10× Taq buffer. The PCR product was digested with NcoI and KpnI and ligated into the vector pTrcHisB, available from Invitrogen, that had been digested with NcoI and KpnI and treated with alkaline phosphatase. The resulting recombinant molecule, referred to herein as pTrc-nCfALN$_{1383}$, was transformed into $E.$ $coli$ strain BL21, available from Novagen Inc., Madison, Wis., to form recombinant cell $E.$ $coli$:pTrc-nCfALN$_{1383}$.

The recombinant cell was grown under standard conditions and then incubated in the presence of 0.5 µM isopropylthio-β-galactoside (IPTG) to induce expression of recombinant protein, predicted to be approximately 50.6 kDa, referred to herein as PCfALN$_{461}$ with an amino acid sequence designated SEQ ID NO:7. Expression was confirmed using Coomassie-blue-stained Tris-glycine gel and by Western blot using an affinity-purified rabbit antibody, the production of which is described in Section D below, which showed expression of an about 52-kDa protein.

A non-full length protein encoded by nucleotides 187–1308 of nCfALN$_{2035}$ was PCR amplified using the pBluescript™ clone described above as the template. PCR reactions were performed as described above using sense primer ALN-FE, having nucleotide sequence 5' GCG GAT CCT ATG CTG AAT TGC AAG AAC CTT G 3', having a BamHI site indicated in bold, designated herein as SEQ ID NO:14, and anti-sense primer ALN-RE, having nucleotide sequence 5' CAG GTA CCC TCT TTT AGA AGC ACC GGT CCC 3', having a KpnI site indicated in bold, designated herein as SEQ ID NO:15. The PCR product, referred to as nCfALN$_{1123}$, with a forward strand designated SEQ ID NO:9 and a reverse strand designated SEQ ID NO:11, was digested with BamHI and KpnI and ligated into the vector pTrcHisB, available from Invitrogen, that had been digested with BamHI and KpnI and treated with alkaline phosphatase. The resulting recombinant molecule, referred to herein as pTrc-nCfALN$_{1123}$, was transformed into $E.$ $coli$ strain BL21, available from Novagen Inc., Madison, Wis., to form recombinant cell $E.$ $coli$:pTrc-nCfALN$_{1123}$.

The recombinant cell was grown under standard conditions and then incubated in the presence of 0.5 µM isopropylthio-β-galactoside (IPTG) to induce expression of recombinant protein, predicted to be approximately 42.2 kDa, referred to herein as PCfALN$_{374}$ with an amino acid sequence designated SEQ ID NO:10. Expression was confirmed using Coomassie-blue-stained Tris-glycine gel and by Western blot using a T7 tag antibody, available from Novagen, which showed expression of an about 55-kDa protein. The protein product was purified by liquid chromatography using a HiTrap™ chelating column charged with $NiCl_2$, available from Pharmacia, and was shown to contain the His tag of the vector when subjected to automated protein sequencing by Edman degradation.

C. Northern Blot Analysis

A Northern Blot analysis was conducted as follows to determine whether allantoinase is expressed exclusively in HMT tissues. HMT tissues were dissected from 1000 adult cat blood-fed $C.$ $felis$ having a male to female ratio of 1:4. Total RNA was separately extracted from HMT tissues and the HMT-less carcasses that resulted from these dissections as follows. The tissues were frozen at −80° C., ground into a powder with a mortar and pestle, and the powders were equally divided into four 2-ml eppendorf tubes each containing 1 ml of lysis buffer. The lysis buffer contained 4 M guanidinium thiocyanate, 25 mM sodium citrate, pH 7.0, 3% sarcosyl, 0.5 M 2-mercaptoethanol, 0.1% antifoam, and 1 mM aurintricarboxylic acid, all available from Sigma Chemical Corporation, St. Louis, Mo. After mixing, the tubes were spun at 14,000 rpm for 2 minutes and the supernatants were transferred to separate 2 ml eppendorf tubes containing 250 µl of phenol, available from Aldrich, Milwaukee, Wis. After mixing, the tubes were spun at 14,000 rpm for 5 minutes and the supernatants were transferred to new 2-ml tubes. This process was repeated 3 times until no proteinaceous matter was visible at the phenol/lysis buffer interface, then 250 µl of chloroform was added to each tube and the contents mixed and spun at 14,000 rpm for 5 minutes followed by transferring the supernatant to a new tube. A volume of isopropanol equal to the volume of the supernatant was added to each tube and the tubes placed on ice for 5 minutes. The tubes were then spun at 14,000 rpm at room temperature for 15 minutes, the supernatants were removed and discarded and the remaining RNA pellets were washed with 70% ethanol and dried. The RNA pellets were resuspended in 100 µl of TE (10 mM Tris, 1 mM ethylenediaminetetraacetic acid (EDTA)). The quantity of RNA in each tube was then determined using a spectrophotometer.

Approximately 10 µg of each RNA was added to separate tubes containing 18.75 µl of loading buffer, which consists of 50% formamide, 16% formaldehyde, 17% water, 7% glycerol, 1×MOPS buffer (a 1:20 dilution of 0.4 M 93-[N-morpholino]propanesulfonic acid (MOPS), 0.1 M sodium acetate, and 20 mM EDTA), 10 µl ethidium bromide, and 10 µl bromophenol blue dye, all available from Sigma. The tubes were heated to 95° C. for 2 minutes then placed on ice. The RNA samples were separated by get electrophoresis on a 1.5% agarose gel with 3.2% formaldehyde and 1×MOPS buffer; the gel was then soaked in water for 30 minutes prior to transfer to remove excess formaldehyde. The gel was then transferred using standard techniques, described by Sambrook et al., ibid, with 10×SSPE as the transfer buffer onto Nytran® nylon membrane, available from Schleicher and Schuell Inc., Keene, N.H. The membrane was UV crosslinked using the Stratalinker®, available from Stratagene, then prehybridized at 42° C. in 50% formamide, 5×SSPE, 1.2% SDS, 5× Denhardt's reagent, 2.5 mM EDTA, and 100 µg/ml salmon sperm DNA. A probe comprising the allantoinase EST nucleic acid molecule, nCfALN$_{682}$ was labeled with α-$^{32}$P-ATP using a DNA labeling kit, available from Amersham and added to the buffer at a concentration of approximately 1×10$^6$ cpm/ml, and allowed to hybridize for 18 hours at 42° C. The blot was then washed as follows: 10 minutes at 42° C. in 4×SSPE and 1% SDS; 10 minutes at 42° C. in 2×SSPE and 1% SDS; 10 minutes at 42° C. with 0.5×SSPE and 0.5×SDS; and 10 minutes at 42° C. with 0.25×SSPE and 0.25% SDS. The blot was then exposed to film for 1 hour, and the film was developed using standard procedures. Analysis of the developed film revealed that allantoinase mRNA was present in HMT tissues but was not present in non-HMT tissues.

Northern Blot analysis was also conducted to determine whether allantoinase mRNA is expressed only in certain stages of the flea life cycle and whether allantoinase mRNA expression is influenced by feeding. Total RNA was extracted as described above from 1000 fleas at each of the following flea life stages: eggs; first instar larvae; third instar larvae; wandering larvae; and pupae; and from 1000 adult fleas under the following feeding conditions: unfed, fed on cat blood for 15 minutes, fed on cat blood for 2 hours, fed on cat blood for 8 hours, and fed on cat blood for 24 hours.

Each RNA sample was separated by gel electrophoresis, transferred to nylon membrane and hybridized with α-$^{32}$P-ATP labeled nCfALN$_{682}$ probe as described above. Analysis of the developed film revealed that allantoinase mRNA was expressed in all adult fleas tested regardless of feeding conditions and was expressed by all life stages except for eggs and pupae, the two life stages which do not feed or excrete urine.

D. Production of Affinity-Purified Antibodies

Affinity-purified rabbit antibodies against a *C. felis* allantoinase protein of the present invention were generated as follows. Rabbits were immunized three times with 50 μg each of recombinant *C. felis* allantoinase protein PCfALN$_{374}$ that was produced as described above and purified by nickel chelating chromatography. The primary immunization was conducted with protein mixed 1:1 in Freund's complete adjuvant and booster immunizations were conducted with protein mixed 1:1 in Freund's incomplete adjuvant. Ten milliliters of rabbit sera were collected each week for 12 weeks and antibodies specific to contaminating *E. coli* proteins were removed by incubation with a piece of nitrocellulose that had been blocked in *E. coli* cell lysate. The decontaminated rabbit serum was then affinity purified using Sepharose 4B beads coupled to purified recombinant *C. felis* allantoinase protein, PCfALN$_{374}$ to produce rabbit antibodies against *C. felis* allantoinase protein PCfALN$_{374}$ (also denoted α-*C. felis* allantoinase antibodies).

A Western blot analysis was conducted using the α-*C. felis* allantoinase antibodies to detect native flea allantoinase protein in flea protein extracts. Nine μg total protein from flea protein extract prepared as described in section E were separated by SDS-PAGE and transferred to a nitrocellulose membrane using standard methods. A 1:1000 dilution of the α-*C. felis* allantoinase antibodies was used as the primary antibody, and a 1:10,000 dilution of alkaline phosphatase conjugated goat α-rabbit IgG, available from Kirkegaard & Perry Laboratories, Gaithersburg, Md., was used as the secondary antibody. The blot detected two distinct bands. The size of each band was approximated using two different protein markers, the SeeBlue™ standard and the Mark12™ standard, each available from Novex, San Diego, Calif. Size approximation based upon the SeeBlue™ standard indicated that the bands were 62 and 65 kDa; and size approximation based upon the Mark12™ standard indicated that the bands were 53 and 55 kDa. These bands are hereinafter referred to as the "53 kDa" and the "55 kDa" bands, respectively.

E. Allantoinase Activity Assay

Allantoinase activity of *C. felis* lysates was assessed by the ability of the lysate to convert allantoin to allantoic acid as follows. Flea protein was extracted from 5.6 grams of unfed adult fleas by grinding fleas into powder using a chilled mortar and pestle followed by suspension in 1×PBS. The mixture was frozen and thawed three times in liquid nitrogen and a 37° C. water bath. The mixture was then sonicated for 60 seconds and centrifuged at 25,000×G for 20 minutes. The supernatant was collected.

The protein concentration of the flea protein extract was adjusted to 0.925 mg/ml with the addition of 1×PBS. Ten μl of this preparation was incubated with 44 μl of 45 mM allantoin and 6 μl of Hepes buffer at room temperature for 20 minutes. The reaction was stopped by the addition of 10 μl of 0.25 N HCl and the mixture was heated to 95° C. for 5 minutes to convert the allantoic acid reaction product into glyoxylic acid and urea. Ten μl of 5 mM 2,4-dinitrophenylhydrazine was added as the colorimetric indicator and the reaction was incubated for 15 minutes at room temperature. One-hundred and twenty μl of 0.5 M sodium phosphate was added and the mixture was incubated at room temperature for 15 minutes. The presence of allantoinase in the flea protein extract was indicated by the conversion of the indicator by glyoxylic acid into dinitrophenylhydrazone, which, following the addition of base had an orange-brown color the absorbance of which was read at 450 nm. Using this method, unfed adult fleas and fleas fed for 24 hours on blood were shown to have similar allantoinase activity. Commercially available peanut allantoinase, available from Sigma, St. Louis, Mo., was used as a positive control and also showed activity using this method.

Acetohydroxamic acid (AHA) a reported allantoinase inhibitor, was tested in the assay. Six μl of AHA, available from Sigma, St. Louis, Mo., was diluted in dimethyl sulfoxide (DMSO) and added to 44 μl of 45 mM allantoin and 10 μl of flea protein extract and the mixture was incubated for 30 minutes at room temperature. An allantoinase activity assay was performed as described above. AHA inhibited flea allantoinase activity in a dose-dependent manner. The IC$_{50}$ and IC$_{90}$ values were measured and determined to be 20 mM and 60 mM, respectively. AHA was also tested for the ability to inhibit peanut allantoinase activity, with nearly identical results.

F. Partial Purification of Native Protein

A partially purified active native *C. felis* allantoinase protein was produced as follows. About 9 milligrams of *C. felis* lysate were passed through a gel filtration column using 1×PBS as the buffer. A Western blot was performed on elution fractions 1–19 using α-*C. felis* allantoinase antibodies prepared as described above. The blot showed a 55 kDa band in fractions 11–17 and a 53 kDa band in fractions 14–19 that were recognized by the antibodies. Activity assays were performed as described above on all elution fractions and only fractions 11–19 showed allantoinase activity.

Fractions having as their major component the 53 kDa band, i.e. fractions 16–19, were combined and further purified by anion exchange chromatography. A Western blot performed on fractions from that chromatography using α-*C. felis* allantoinase antibodies detected a 53 kDa band in fractions 6–9. All fractions were tested for activity and only fractions 6–9 were shown to have allantoinase activity. Fractions 6–9 were combined and further purified by affinity column chromatography using an affinity column constructed by coupling approximately 1 mg of α-*C. felis* allantoinase antibodies to Sepharose 4B beads. Elution fractions 1–5 showed activity, with the greatest allantoinase activity in the first fraction; fractions which eluted after fraction 5 showed no activity. The first fraction was subjected to SDS-PAGE followed by silver staining which showed a nearly pure 53 kDa protein band. Fractions 1–5 were combined and concentrated using a Centricon Plus-20 concentrator and subjected to Western blot analysis using α-*C. felis* allantoinase antibodies which revealed a single 53 kDa band.

Elution fractions from the gel filtration column having as their major component the 55 kDa band, i.e. fractions 12–15, were combined and further purified by cation exchange chromatography. A Western blot performed on fractions 3–6 from that chromatography using α-*C. felis* allantoinase antibodies detected a 55 kDa band. Fractions 3–6 were tested and shown to have allantoinase activity. Fractions which did not contain the 55 kDa band did not exhibit allantoinase activity.

G. Protein Localization Study

Protein localization in thin sections of fleas was conducted using immunohistochemistry as follows. Unfed adult fleas were fixed in paraformaldehyde, imbedded with paraffin, thin sectioned and fixed onto glass cover slips using standard techniques. A 1:1000 dilution of serum containing rabbit α-C. *felis* allantoinase antibodies, produced as described above, was used in combination with a 1:10,000 dilution of anti-rabbit secondary antibody, from a StrAvi-Gen™ Super Sensitive Immunodetection System and substrate from an AEC Substrate Pack, each available from Bio Genex, San Ramon, Calif. for localization of the native protein within the thin sections. This localization procedure revealed that allantoinase protein is present in the Malpighian tubules, hindgut and rectum of adult fleas, and is not present in other tissues of the flea. The same procedure was conducted using normal rabbit sera diluted 1:500 as a negative control and no staining of tissues was observed.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

---

What is claimed is:

1. An isolated *Ctenocephalides felis* protein encoded by a nucleic acid molecule that hybridizes to a polynucleotide with a nucleic acid sequence selected from the group consisting of SEQ ID NO:3, SEQ ID NO:5, SEQ ID NO:8 and SEQ ID NO:11, under conditions comprising: (1) hybridizing in a solution comprising 1×SSC in the absence of helix destabilizing compounds, at a temperature of about 37° C.; and (2) washing in a solution comprising 1×SSC and in the absence of helix destabilizing compounds, at a temperature of about 47.5° C., wherein said isolated protein has allantoinase activity.

2. The protein of claim 1, wherein said nucleic acid molecule is selected from the group consisting of SEQ ID NO:1, SEQ ID NO:4, SEQ ID NO:6, SEQ ID NO:9 and fragments thereof, wherein said fragment comprises at least 25 contiguous nucleotides from a nucleic acid sequence selected from the group consisting of SEQ ID NO:1, SEQ ID NO:4, SEQ ID NO:6, and SEQ ID NO:9 and encodes a protein having allantoinase activity.

3. The protein of claim 1, wherein said protein comprises an amino acid sequence selected from the group consisting of SEQ ID NO:2, SEQ ID NO:7, SEQ ID NO:10, and fragments thereof, wherein said fragment has allantoinase activity.

4. A composition comprising an excipient and an isolated *Ctenocephalides felis* protein encoded by a nucleic acid molecule that hybridizes to a polynucleotide with a nucleic acid sequence selected from the group consisting of SEQ ID NO:3, SEQ ID NO:5, SEQ ID NO:8 and SEQ ID NO:11, under conditions comprising: (1) hybridizing in a solution comprising 1×SSC in the absence of helix destabilizing compounds, at a temperature of about 37° C.; and (2) washing in a solution comprising 1×SSC and in the absence of helix destabilizing compounds, at a temperature of about 47.5° C., wherein said isolated protein has allantoinase activity.

5. The composition of claim 4, wherein said nucleic acid molecule is selected from the group consisting of SEQ ID NO:1, SEQ ID NO:4, SEQ ID NO:6, SEQ ID NO:9 and fragments thereof, wherein said fragment comprises at least 25 contiguous nucleotides from a nucleic acid sequence selected from the group consisting of SEQ ID NO:1, SEQ ID NO:4, SEQ ID NO:6, and SEQ ID NO:9 and encodes a protein having allantoinase activity.

6. The composition of claim 4, wherein said protein comprises an amino acid sequence selected from the group consisting of SEQ ID NO:2, SEQ ID NO:7, SEQ ID NO:10, and fragments thereof, wherein said fragment has allantoinase activity.

7. The composition of claim 4, wherein said composition further comprises a component selected from the group consisting of an adjuvant and a carrier.

8. A method to detect an inhibitor of flea allantoinase activity, said method comprising: (a) contacting an isolated protein of claim 1 with a putative inhibitory compound under conditions in which, in the absence of said compound, said protein has activity; and (b) determining if said putative inhibitory compound inhibits said activity.

9. The method of claim 8, wherein said nucleic acid molecule is selected from the group consisting of SEQ ID NO:1, SEQ ID NO:4, SEQ ID NO:6, SEQ ID NO:9 and fragments thereof, wherein said fragment comprises at least 25 contiguous nucleotides from a nucleic acid sequence selected from the group consisting of SEQ ID NO:1, SEQ ID NO:4, SEQ ID NO:6, and SEQ ID NO:9 and encodes a protein having allantoinase activity.

10. The method of claim 8, wherein said protein comprises an amino acid sequence selected from the group consisting of SEQ ID NO:2, SEQ ID NO:7, SEQ ID NO:10, and fragments thereof, wherein said fragment has allantoinase activity.

11. An isolated *Ctenocephalides felis* protein comprising an amino acid sequence selected from the group consisting of SEQ ID NO:2, SEQ ID NO:7, and SEQ ID NO:10 and variants thereof that are at least 95% identical to an amino acid sequence selected from the group consisting of SEQ ID NO:2, SEQ ID NO:7, and SEQ ID NO:10, wherein said protein has allantoinase activity.

12. The protein of claim 11, wherein said protein is encoded by a nucleic acid molecule selected from the group consisting of SEQ ID NO:1, SEQ ID NO:4, SEQ ID NO:6, SEQ ID NO:9 and fragments thereof, wherein said fragment comprises at least 25 contiguous nucleotides from a nucleic acid sequence selected from the group consisting of SEQ ID NO:1, SEQ ID NO:4, SEQ ID NO:6, and SEQ ID NO:9 and encodes a protein having allantoinase activity.

13. The protein of claim 11, wherein said protein comprises an amino acid sequence selected from the group consisting of SEQ ID NO:2, SEQ ID NO:7, and SEQ ID NO:10.

14. A kit comprising the isolated protein of claim 1.

15. The kit of claim 14, wherein said nucleic acid molecule is selected from the group consisting of SEQ ID NO:1, SEQ ID NO:4, SEQ ID NO:6, SEQ ID NO:9 and fragments thereof, wherein said fragment comprises at least 25 contiguous nucleotides from a nucleic acid sequence selected from the group consisting of SEQ ID NO:1, SEQ ID NO:4, SEQ ID NO:6, and SEQ ID NO:9 and encodes a protein having allantoinase activity.

16. The kit of claim 14, wherein said protein comprises an amino acid sequence selected from the group consisting of SEQ ID NO:2, SEQ ID NO:7, SEQ ID NO:10, and fragments thereof, wherein said fragment has allantoinase activity.

* * * * *